United States Patent
Rincon et al.

(10) Patent No.: US 10,655,126 B2
(45) Date of Patent: May 19, 2020

(54) METHODS AND COMPOSITIONS TO TREAT DRUG-INDUCED DISEASES AND CONDITIONS

(71) Applicants: University of Vermont and State Agricultural College, Burlington, VT (US); Asociacion Centro de Investigacion Cooperativa en Biociencias-CIC bioGUNE, Derio (ES)

(72) Inventors: Mercedes Rincon, Burlington, VT (US); Maria Luz Martinez Chantar, Derio (ES); Juan Anguita, Derio (ES); Oliver Dienz, Shelburne, VT (US)

(73) Assignees: University of Vermont and State Agricultural College, Burlington, VT (US); Asociacion Centro de Investigacion Cooperativa en Biociencias-CIC bioGune, Derio (ES)

( * ) Notice: Subject to any disclaimer, the term of this patent is extended or adjusted under 35 U.S.C. 154(b) by 0 days.

(21) Appl. No.: 15/743,096

(22) PCT Filed: Jul. 9, 2016

(86) PCT No.: PCT/US2016/041663
§ 371 (c)(1),
(2) Date: Jan. 9, 2018

(87) PCT Pub. No.: WO2017/011356
PCT Pub. Date: Jan. 19, 2017

(65) Prior Publication Data
US 2019/0078086 A1 Mar. 14, 2019

Related U.S. Application Data

(60) Provisional application No. 62/324,584, filed on Apr. 19, 2016, provisional application No. 62/190,803, filed on Jul. 10, 2015.

(51) Int. Cl.
| | | |
|---|---|---|
| *C12N 15/11* | (2006.01) | |
| *C12N 15/113* | (2010.01) | |
| *A61K 31/7105* | (2006.01) | |
| *C07K 16/40* | (2006.01) | |

(52) U.S. Cl.
CPC ........ *C12N 15/113* (2013.01); *A61K 31/7105* (2013.01); *C07K 16/40* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,922,567 A | 7/1999 | Au-Young et al. |
| 6,001,598 A | 12/1999 | Au-Young et al. |
| 6,043,222 A | 3/2000 | Au-Young et al. |
| 6,222,029 B1 | 4/2001 | Edwards et al. |
| 6,916,609 B1 | 7/2005 | Au-Young et al. |
| 6,949,544 B2 | 9/2005 | Bethiel et al. |
| 8,354,237 B2 | 1/2013 | Rincon et al. |
| 8,445,648 B2 | 5/2013 | Rincon et al. |
| 2002/0098511 A1 | 7/2002 | Heichman et al. |
| 2008/0261217 A1 | 10/2008 | Milnikov et al. |
| 2010/0129931 A1* | 5/2010 | Rincon ............... C07K 16/18 436/501 |
| 2012/0165269 A1 | 6/2012 | Kim |
| 2015/0202257 A1 | 7/2015 | Rincon et al. |
| 2018/0125930 A1 | 5/2018 | Rincon et al. |

FOREIGN PATENT DOCUMENTS

| | | |
|---|---|---|
| WO | 2006068440 A | 6/2006 |
| WO | 2008097467 A1 | 8/2008 |
| WO | 2009134370 A3 | 11/2009 |
| WO | 2014011742 A1 | 1/2014 |

OTHER PUBLICATIONS

George, J. et al., "Differential Effects of Anti-B2-Glycoprotein I Antibodies on Endothelial Cells and on the Manifestations of Experimental Antiphospholipid Syndrome." American Heart Association, 1998, vol. 97, pp. 900-906.
Giusti, A. et al., "Somatic diversification of S107 from an antiphosphocholine to an anti-DNA autoantibody is due to a single base change in its heavy chain variable region." Proc. Natl. Acad. Sci. USA, May 1987, vol. 84, pp. 2926-2930.
Gottesman, M. et al., "Multidrug Resistance in Cancer: Role of ATP-Dependent Transporters." Nature Reviews Cancer, Jan. 2002, vol. 2, pp. 48-58.
Gussow, D. et al., "Humanization of Monoclonal Antibodies." Methods in Enzymology, 1991, vol. 203, pp. 99-121.
Guy, C.T., et al., "Induction of Mamary Tumors by Expression of Polyomavirus Middle T Oncogene: A Transgenic Mouse Model for Metastatic Disease." Mol. Cell. Biol.(1992), vol. 12(3), pp. 954-961.
Halazonetis, T. et al., "c-Jun Dimerizes with Itself and with c-Fos, Forming Complexes of Different DNA Binding Affinities." Cell, Dec. 2, 1988, vol. 55, pp. 917-924.
Hamanaka, RB. and Chan Del, N. S., "Mitochondrial reactive oxygen species regulate cellular signaling and dictate biological outcomes." Trends Biochem Sci, Sep. 2010, vol. 35, pp. 505-513.

(Continued)

*Primary Examiner* — Ekaterina Poliakova-Georgantas
(74) *Attorney, Agent, or Firm* — Pierce Atwood LLP

(57) ABSTRACT

Methods and compounds useful to treat drug-induced diseases and conditions are provided. Methods of administering one or more MCJ-inhibiting compounds to decrease MCJ polypeptide activity in cells, tissues, and/or subjects as a treatment for a drug-induced disease or condition are provided.

14 Claims, 7 Drawing Sheets
Specification includes a Sequence Listing.

(56) References Cited

OTHER PUBLICATIONS

Harbottle, A. et al., "Role of Glutathione S-Transferase P1, P-Glycoprotein and Multidrug Resistance-Associated Protein 1 in Acquired Doxorubicin Resistance." Int J Cancer, Jun. 15, 2001, vol. 92, pp. 777-783.
Harker, W. et al., "Multidrug (Pleiotropic) Resistance in Doxorubicin-selected Variants of the Human Sarcoma Cell f-ine MES-SA." Cancer Research, Sep. 1985, vol. 45, pp. 4091-4096.
Hatle, K. et al., "Methylation-controlled J protein promotes c-Jun degradation to prevent ABCB1 transporter expression." Molecular and Cellular Biology, American Society for Microbiology, vol. 27, No. 8, Apr. 1, 2007, pp. 2952-2966.
Hatle, K., et al., "MCJ/DnaJC15 an Endogenous Mitochondrial Repressor of the Respiratory Chain that Controls Metabolic Alterations." Mol. Cell. Biol. (2013), vol. 33, No. 11, pp. 2302-2314.
Hayashi, M. et al., "A crucial role of mitochondrial Hsp40 in preventing dilated cardiomyopathy." Nat Med, Jan. 2006, vol. 12, pp. 128-132.
Hogquist, K.A. et al., "T cell receptor antagonist peptides induce positive selection." Cell, Jan. 1994, vol. 76, pp. 17-27.
Holm, P. et al., "Functional mapping and single chain construction of the anti-cytokeratin 8 monoclonal antibody TS1." Molecular Immunology, Feb. 2007, vol. 44, pp. 1075-1084.
Horton, et al., "Mitochondria-Penetrating Peptides." Chemistry & Biology (2008), vol. 15(4); pp. 375-382.
Hosoda, A., et al., "Positive contribution of ERdj5/JPDI to endoplasmic reticulum protein quality control in the salivary," Biochem J, Sep. 2009, vol. 425, pp. 117-125.
Hu, YB and XY Liu, "Protective effects of SP600125 in a diet-induced rat model of non-alcoholic steatohepatitis." Scand J Gastroenlerol., 2009, vol. 44, pp. 1356-1362. (Abstract only, 1 page).
Hunter, P.J. et al., "Mrj encodes a DnaJ-related co-chaperone that is essential for murine placental development." Development, Mar. 1999, vol. 126, pp. 1247-1258.
Huston et al., "Protein engineering of antibody binding sites: Recovery of specific activity in an anti-digoxin single-chain Fv analogue produced in *Escherichia coli*." Proc. Natl. Acad. Sci. USA, 85, (1988); pp. 5879-5883.
International Preliminary Report on Patentability and the Written Opinion from the International Searching Authority dated Aug. 22, 2017 from PCT/US2016/018406, 8 pages.
International Preliminary Report on Patentability and the Written Opinion from the International Searching Authority dated Aug. 4, 2009 from PCT/US2008/001357, 10 pages.
International Preliminary Report on Patentability and the Written Opinion from the International Searching Authority dated Jan. 13, 2015 from PCT/US2013/049885, 7 pages.
International Search Report and the Written Opinion of the International Searching Authority dated Jun. 6, 2008 for International Patent Application No. PCT/US2008/001357.
International Search Report and the Written Opinion of the International Searching Authority dated Oct. 21, 2013 for International Patent Application No. PCT/US2013/049885.
International Search Report and Written Opinion from corresponding international application PCT/US2016/041663 dated Feb. 15, 2017.
International Preliminary Report on Patentability from corresponding international application PCT/US2016/041663 dated Jan. 25, 2018.
International Search Report dated Aug. 25, 2016 from PCT/US2016/018406, 6 pages.
Izadi, et al., "Innate immune responses to B. burgdorderi mediated by JNK1 and the cochaperone, methylation controlled DNAJ (MCJ)." Disseration for Doctor of Philosphy, Department of Veterinary & Animal Sciences, University of Massachusetts,—Amherst, MA USA, 2011, pp. 1-85.
Izawa, I., et al., "Identification of Mrj, a DnaJ/Hsp40 Family Protein, as a Keratin 8/18 Filament Regulatory Protein." Journal of Biological Chemistry, Nov. 3, 2000, Vo. 275, pp. 34521-34527.
Kampinga, H.H. et al., "Guidelines for the nomenclature of the human heat shock proteins." Cell Stress Chaperones, Jan. 2009, vol. 14, pp. 105-111.
Kawakami, K. et al., "Identification and purification of a human immunoglobulin-enhancer-binding protein (NF-KB) hat activates transcription from a human immunodeficiency virus type 1 promoter in vitro." Proc Natl Acad Sci. USA, Jul. 1988, vol. 85, pp. 4700-4704.
Khalil, AA. et al., "Heat shock proteins in oncology: diagnostic biomarkers or therapeutic targets"? Biochimica et Biophysica Acta (BBA)—Reviews on Cancer, Dec. 2011, vol. 1816, pp. 89-104.
Klement, G. et al., "Differences in Therapeutic Indexes of Combination Metronomic Chemotherapy and an Anti-VEGFR-2 Antibody in Multidrug-resistant Human Breast Cancer Xenografts." Clinical Cancer Research, Jan. 2002, vol. 8, pp. 221-232.
Kohler, G., et al., "Derivation of specific antibody-producing tissue culture and tumor lines by cell fusion." Eur J Immunol., Jul. 1976, vol. 6, pp. 511-519.
Koppenol, W.H. et al., "Otto Warburg's contributions to current concepts of cancer metabolism." Nat Rev Cancer, May 2011, vol. 11, pp. 325-337.
Landschulz, W. et al., "The DNA Binding Domain of the Rat Liver Nuclear Protein C/EBP is Bipartite." Science, Mar. 31, 1989, vol. 243, pp. 1681-1688.
Lapuente-Brun, E. et al., "Supercomplex Assembly Determines Electron Flux in the Mitochondrial Electron Transport Chains." Science (2013), vol. 340, pp. 1567-1570.
Leachman, S. et al., "First-in-human Mutation-targeted siRNA Phase lb Trial of an Inherited Skin Disorder." American Society of Gene & Cell Therapy, Feb. 2010, vol. 18, gs. 442-446.
Lee, D. et al., "Involvement of the Molecular Chaperone Ydj1 in the Ubiquitin-Dependent Degradation of Short-Lived and Abnormal Proteins in *Saccharomyces cerevisiae*." Molecular Cell Biology, Sep. 1996, vol. 16, pp. 4773-4781.
Lee, W. et al., "Purified Transcription Factor AP-1 Interacts with TPA-Inducible Enhancer Elements." Cell, Jun. 19, 1987 , vol. 49, pp. 741-752.
Levine, A.J. and Puzio-Kuter, A.M., "The control of the metabolic switch in cancers by oncogenes and tumor suppressorgenes." Science, Dec. 2010, vol. 330, pp. 1340-1344.
Lindsey, J. et al., "Epigenetic inactivation of MCJ (DNAJD1) in malignant paediatric brain tumors" Int J Cancer, Jan. 15, 2006, vol. 118, pp. 346-352.
Lingzhou et al., "Advances in research on targeting mitochondria for cancer therapy." Anhui Medical and Pharmaceutical, vol. 15, No. 11, 1329-1331.
Lo et al., "Tid1, a cochaperone of the heat shock 70 protein and the mammalian counterpart of the *Drosophila* tumor suppressor l(2)tid, is critical for early embryonic development and cell survival." Mol. Cell. Biol. Mar. 2004, vol. 24, pp. 2226-2236.
Longley, D.B. et al., "Molecular mechanisms of drug resistance." Journal of Pathology, Jan. 2005, vol. 205, pp. 275-292.
MacCallum, R. et al., "Antibody-antigen Interactions: Contact Analysis and Binding Site Topography." Journal of Molecular Biology, Oct. 11, 1996, vol. 262, pp. 732-745.
Maines, T. R et al., "Transmission and pathogenesis of swine-origin 2009 A(H1N1) influenza viruses in ferrets and mice" Science, Jul. 2009, vol. 325, pp. 484-487.
Mariuzza, RA et al., "The Structural Basis of Antigen-Antibody Recognition." Annu. Rev. Biophys., Biophys. Chem., 1987, vol. 16, pp. 139-159.
McGill et al., "The mechanism underlying acetaminophen-induced hepatotoxicity in humans and mice involves mitchondrial damage and nuclear DNA fragmentation." Journal of Clinical Investigation (2012), vol. 122, No. 4, pp. 1574-1583.
McKenzie, M. and Ryan, M.T., "Assembly factors of human mitochondrial complex I and their defects in disease." UBMB Life, Jul. 2010, vol. 62, pp. 497-502.

(56) References Cited

OTHER PUBLICATIONS

Villa et al., "Neoangiogenesis-related genese are hallmarks of fast-growing hepatocellular carcinomas and worse survival. Results from a prospective study." Gut. 2016;65:861-869, doi: 10.1136/gutjnl-2014-308483.
Wahl, R. et al., "Improved Radioimaging and Tumor Localization with Monoclonal F(ab')2.", Journal of Nuclear Medicine., Apr. 1983, vol. 24, pp. 316-325.
Walsh, P. et al., "The J-protein family: modulating protein assembly, disassembly and translocation." EMBO Rep, Jun. 2004, vol. 5, pp. 567-571.
Wang, et al., "The brown fat-enriched secreted factor Nrg4 preserves metabolic homeostasis through attenuation of hepatic lipogenesis." Nature Medicine (2014), 20, pp. 1436-1445.
Warburg, J., "On Respiratory Impairment in Cancer Cells." Science, Aug. 10, 1956, vol. 124, pp. 267-272.
Watts, J. and D Corey, "Silencing disease genes in the laboratory and the clinic", Journal of Pathology, 2012, vol. 226, pp. 365-379.
Winkler, K et al., "Changing the Antigen Binding Specificity by Single Point Mutations of an Anti-p24 (HIV-1) antibody." Journal of Immunology, Oct. 15, 2000, vol. 165, pp. 4505-4514.
Witham, J. et al., "Transient ectopic expression as a method to detect genes conferring drug resistance." International Journal of Cancer, vol. 122, No. 11, Jan. 1, 2008, pp. 2641-26A16745.
Wu, H. et al., "Humanization of a Murine Monoclonal Antibody by Simultaneous Optimization of Framework and CDR Residues." J. Mol. Biol., Nov. 19, 1999, vol. 294, pp. 151-162.
Yang, ZX, et al., "Effects of nuclear receptor FXR on the regulation of liver lipid metabolism in patients with non-alcoholic fatty liver disease." Hepatol Int, 2010, vol. 4, pp. 741-748.
Yin et al., "Silencing heat shock factor 1 by small interfering RNA abrogates heat shock-induced cardioprotection against ischemia-reperfusion injury in mice." Journal of Molecular and Cellular Cardiology (2005) vol. 39(4), pp. 681-689.
Young, J. et al., "More than folding: localized functions of cytosolic chaperones." Trends in Biochemical Science, Oct. 2003, vol. 28, pp. 541-547.
Zhang, J. et al., "Osthole improves alcohol-induced fatty liver in mice by reduction of hepatic oxidative stress." Phytother Res., May 2011, vol. 25, pp. 638-643. (Abstract only, 1 p.).
Zhu, F. et al., "COOH-terminal Src Kinase-Medicated c-Jun Phosphorylation Promotes c-Jun Degradation and Inhibits Cell Transformation." Cancer Research, Jun. 1, 2006, vol. 66, pp. 5729-5736.
Acin-Perez, R., et al., "Respiratory Active Mitochondrial Supercomplexes." Mol. Cell. 32, (2008); pp. 529-539.
Addya, S. et al., "Targeting of NH2-terminal-processed Microsomal Protein to Mitochondria: A Novel Pathway for the Biogenesis of Hepatic Mitochondrial P450MT2." The Journal of Cell Biology, Nov. 3, 1997, vol. 139, pp. 589-599.
Affidavit Regarding Deposited Microorganism Pursuant to 37 C.F.R 1.808 filed in U.S Appl. No. 12/449,265.
Ahn, BY et al., "Tid1 is a new regulator of p53 mitochondrial translocation and apoptosis in cancer" Oncogene, Feb. 2010, vol. 29, pp. 1155-1166.
Alakhova, E.Y., et al., "Differential Metabolic Responses to Pluronic in MDR and non-MDR Cells: A Novel Pathway or Chemosensitization of Drug Resistant Cancers." J. Control Release (2010), 142(1), pp. 89-100.
Alley, M. et al., "Feasibility of Drug Screening with Panels of Human Tumor Cell Lines Using a Micoculture Wetrazolium Assay", Cancer Research, Feb. 1, 1988, vol. 48, pp. 589-601.
Alverez-Calderon, M.A., et al., "Tyrosine Kinase Inhibition in Leukemia Induces an Altered Metabolic State Sensitive to Mitochondrial Perurbations." Clin. Cancer Res. 21(6), (2015); pp. 1360-1372.
Angel, P. et al., "Phorbol Ester-Inducible Genes Contain a Common Cis Element Recognized by a TPA-Modulated Wrans-Acting Factor." Cell, Jun. 19, 1987, vol. 49, pp. 729-739.
Araki, K. et al., "mTOR regulates memory CD8 T cell differentiation." Nature, Jul. 2009, vol. 460, pp. 108-112.
Auphan, N. et al., "Consequences of intrathymic TCR engagement by partial agonist on selection events and peripheral T cell activation program" J Immunol, May 1998, vol. 160, pp. 4810-4821.
Baerga-Ortiz et al., "Epitope mapping of a monoclonal antibody against human thrombin by H/D-exchange mass specgtromBIRD et al., "Single-Chain Antigen-Binding Proteins." Science 242, (1988); pp. 423-426etry reveals selection of a diverse sequence in a highly conserved protein." Protein Science 11, (2002), pp. 1300-1308.
Barbier-Torres et al., "Stabilization of LKB1 and Akt by neddylation regulates energy metabolism in liver cancer." Oncotarget (2015) 6(4), 2509-2423.
Bird, R., et al, "Single-Chain Antigen-Binding Proteins." Science, Oct. 21, 1988, vol. 242, pp. 423-426.
Brummelkamp, T. et al., "A System for Stable Expression of Short Interfering RNAs in Mammalian Cells." Science, Apr. 19, 2002, vol. 296, pp. 550-553.
Cairns, R.A. et al., "Regulation of cancer cell metabolism." Nat Rev Cancer, Feb. 2011, vol. 11, pp. 85-95.
Caldas C. et al., "Humanization of the anti-CD18 antibody 6. 7: an unexpected effect of framework residue in binding to antigen." Molecular Immunology, May 2003, vol. 39, pp. 941-952.
Campbell, A., Monoclonal Antibody Technology, Laboratory Techniques in Biochemistry and Molecular Biology, 1984, Elsevier Science Publishers BV.: Amsterdam, The Netherlands vol. 13, pp. 1-32, Chapter 1: General Properties and Applications of Monoclonal Antibodies.
Casset, F. et al., "A peptide mimetic of an anti-CD4 monoclonal antibody by rational design." Biochemical and Biophysical Research Communication, Jul. 18, 2003, vol. 307, pp. 198-205.
Chen, Y. et al., "Characterization of Adriamycin-resistant Human Breast Cancer Cells Which Display Overexpression of a Novel Resistance-related Membrane Protein." Journal of Biological Chemistry, Jun. 15, 1990, vol. 265, pp. 10073-10080.
Chen, Y. et al., "In Situ Biochemical Demonstration that P-Glycoprotein Is a Drug Efflux Pump with Broad Specificity." Journal of Cellular Biology, Mar. 6, 2000, vol. 148, pp. 863-870.
Chien, N. et al., "Significant structural and functional change of an antigen-binding site by a distant amino acid Substitution: Proposal of a structural mechanism." Pree. Natl. Acad. Sci., USA, Jul. 1989, vol. 86, pp. 5532-5536.
Clason, T. et al., "The structure of eukaryotic and prokaryotic complex I." J Struct Biol, Jan. 2010, vol. 169, pp. 81-88.
Comerford, K.et al., "Hypoxia-inducible Factor-1-dependent Regulation of the Multidrug Resistance (MDR1) Gene." Cancer Research, Jun. 15, 2002, vol. 62, pp. 3387-3394.
Conze et al., "Autocrine p/Production of Interleukin 6 Causes Multidrug Resistance in Breast Cancer Cells." Cancer Research, Dec. 15, 2001, vol. 61, pp. 8851-8858.
Conze, D. et al., "c-Jun NH(2)-terminal kinase (JNK)1 and JNK2 have distinct roles in COB(+) T cell activation." J Exp Med, Apr. 2002, vol. 195, pp. 811-823.
Craig, EA et al., "The diverse roles of J-proteins, the obligate Hsp70 co-chaperone." Rev Physiol Biochem Pharmacol., 2006, vol. 156, pp. 1-21.
Czauderna et al., "Structural variations and stabilizing modifications of synthetic siRNAs in mammalian cells." Nucleic Acids Research, 2003 vol. 31, No. 11, 2705-2716.
Da Cruz, S. et al., "Proteomic analysis of the mouse liver mitochondrial inner membrane." J. Biol. Chem., Oct. 2003, vol. 278, pp. 41566-41571.
De Pascalis, R et al., "Grafting of "Abbreviated" Complementary-Determining Regions Containing Specificity-Determining Residues Essential for Ligand Contact to Engineer a Less immunogenic Humanized Monoclonal Antibody." Journal of Immunology, 2002, vol. 169, pp. 3076-3084.
Del Gaizo, V. et al., "Targeting proteins to mitochondria using TAT." Molecular Genetics and Metabolism, 2003, vol. 80, pp. 170-180.
Derijard, B. et al., "JNK1: A Protein Kinase Stimulated by UV Light and Ha-Ras That Binds and Phosphorylates the c-Jun Activation Domain." Cell., Mar. 25, 1994, vol. 76, pp. 1025-1037.
Devincenzo et al., "A randomized, double-blind, placebo-controlled study of an RNAi-based therapy directed against respiratory syncytial virus." PNAS, May 11, 2010, vol. 107, pp. 8800-8805.

(56) References Cited

OTHER PUBLICATIONS

Diah, S. et al., "Resistance to Mitoxantrone in Multidrug-resistant MCF7 Breast Cancer Cells: Evaluation of Mitoxantrone Transport and the Role of Multidrug Resistance Protein Family Proteins." Cancer Research, Jul. 15, 2001, vol. 61, pp. 5461-5467.
Diekert, K. et al., "An internal targeting signal directing proteins into the mitochondrial intermembrane space." PNAS Oct. 12, 1999, vol. 96, pp. 11752-11757.
Doyle, L et al., "Multidrug resistance mediated by the breast cancer resistance protein BCRP (ABCG2)." Oncogene, Oct. 20, 2003, vol. 22, pp. 7340-7358.
Dykxhoorn, D.M. et al., "The silent treatment: siRNAs as small molecule drugs." Gene Therapy, 2006, vol. 13, pp. 541-552.
Ehrlich, M. et al., "Hypomethylation and hypermethylation of DNA in Wilms tumors", Oncogene, Sep. 26, 2002, vol. 21, pp. 6694-6702.
Fairchild, C. et al., "Isolation of Amplified and Overexpressed DNA Sequences from Adriamycin-resistant Human Breast Cancer Cells". Cancer Research, Oct. 1, 1987, vol. 47, pp. 5141-5148.
Fairchild, C. et al., "Multidrug Resistance in Cells Transfected with Human Genes Encoding a Variant Pglycoprotein and Glutathione S-Transferase-n." Molecular Pharmacology, Jun. 1990, vol. 37, pp. 801-809.
Fang, D. et al., "Ubiquitin-mediated fluorescence complementation reveals that Jun ubiquitinated by Itch/AIP4 is localized to lysosomes." Proc Natl Acad Csi US A, Oct. 12, 2004, vol. 101, pp. 14782-14787.
Fernandez-Alvarez et al., "TRAIL-producing NK cells contribute to liver injury and related fibrogenesis in the context of GNMT deficiency." Lab Invest. (2015), 95, pp. 223-236.
Finlay, D and Cantrell, DA., "Metabolism, migration and memory in cytotoxic T cells." Nat Rev Immunol, Feb. 2011, vol. 11, pp. 109-117.
Fuchs, S. et al., "Phosphorylation-dependent targeting of c-Jun ubiquitination by Jun N-kinase." Oncogene, Oct. 3, 1996, vol. 13, pp. 1531-1535.
Gao et al., "Jun Turnover is Controlled Through JNK-Dependent Phosphorylation of the E3 Ligase Itch." Science (2004), vol. 306, Issue 5694.
Garcia-Ruiz, C. et al., "Metabolic therapy: lessons from liver diseases." Curr Pharm Des., Dec. 2011, vol. 17, pp. 3933-3944. (Abstract only, 1 page).
Genbank Submission; NIH, Accession No. AAH95400, Strausberg et al.; May 6, 2005.
Genbank Submission; NIH/NCBI, Accession No. AAD38506; Shridhar et al.; May 25, 2001, 2 pages.
Genbank Submission; NIH/NCBI, Accession No. AF126743; Shridhar et al.; May 25, 2001, 2 pages.
Genbank Submission; NIH/NCBI, Accession No. NP_037370; Hendrickson et al.; Jul. 29, 2011, 2 pages.
Genkbank Submission; NIH, Accession No. BC095400, Strausberg et al., May 6, 2005.
Mechetner, E et aL, "Levels of Multidrug Resistance (MDR1) P-Glycoprotein Expression by Human Breast Cancer Correlate within in Vitro Resistance to Tazol and Doxorubicin." Clinical Cancer Research, Feb. 1998, vol. 4, pp. 389-398.
Mitra, A et al., "Multi-faceted role of HSP40 in cancer." Clin Exp Metastasis, 2009, vol. 26, pp. 559-567.
Mokranjac, D. et al., "The import motor of the yeast mitochondrial TIM23 preprotein translocase contains two different J proteins, Tim14 and Mdj2." J Biol Chem, Sep. 2005, vol. 280, pp. 31608-31614.
Mokranjac, D. et al., "Tim14, a novel key component of the import motor of the TIM23 protein translocase of mitochondria." EMBO Journal, Oct. 1, 2003, vol. 22, pp. 4945-4956.
Musti, A et al., "Differential Regulation of c-Jun and Juno by Ubiquitin-Dependent Protein Degradation." Biol Chem., Oct. 1996, vol. 377, pp. 619-624.
Musti, A. et al., "Reduced Ubiquitin-Dependent Degradation of c-Jun After Phosphorylation by MAP Kinases." Science, Jan. 17, 1997, vol. 275, pp. 400-402.
Nabhan J. et al. "The 19 S Proteasomal Subunit POH1 Contributes to the Regulation of c-Jun Ubiquitination, Stability, and Subcellular Localization." Journal of Biological Chemistry, Jun. 9, 2006, vol. 281, pp. 16099-16107.
Nambudiri, et al., "Small Interfering RNA." Journal of Investigative Dermatology (2013), 133: e15 doi: 10.1038/id.2013.411.
Nateri, A. et al., "The Ubiquitin Ligase SCFFbw7 Antagonizes Apoptotic JNK Signaling." Science, Feb. 27, 2004, vol. 303, pp. 1374-1378.
Navasa et al., "Regulation of Oxidative Stress by Methylation-Controlled J Protein Controls Macrophage Responses to Inflammatory Insults." Journal of Infectious Diseases (2014), vol. 211, No. 1, pp. 135-145.
Negro, Francesco, "Mechanisms and significance of liver steatosis in hepatitis C virus infection." World Journal of Gastroenterology, Nov. 14, 2006, vol. 12, pp. 6756-6765.
Non-Final Office Action for U.S Appl. No. 12/449,265 dated Jan. 5, 2012, 46 pages.
Noonan, K.E. et al., "Quantitative analysis of MDR1(multidrug resistance) gene expression in human tumors by Dloymerase chain reaction." Proc Natl Acad Sci. USA, Sep. 1990, vol. 87, pp. 7160-7164.
Ohnishi, T. et al., "Structure-function studies of iron-sulfur clusters and semiquinones in the NADH-Q oxidoreductase segment of the respiratory chain." Biochim Biophys Acta, Jun. 1998, vol. 1365, pp. 301-308.
Orthwein, A. et al., "Optimal functional levels of activation-induced deaminase specifically require the Hsp40 DnaJa1." EMBO J, Feb. 2012, vol. 31, pp. 679-691.
Pedraza-Alva et al.,Activation of p38 MAP kinase by DNA double-strand breaks in V(D)J recombination induces a G2/M cell cycle checkpoint the EMBO Journal 2006, pp. 763-773.
Phillips, A., "The challenge of gene therapy and DNA delivery." J. Pharm Pharmacology (2001) 53, pp. 1169-1174.
Pirollo et al., "Targeted Delivery of Small Interfering RNA: Approaching Effective Cancer Therapies." Cancer Res. (2008), 68(5), pp. 1247-1250.
Plavinskaya, T. et al., "Effects of acute and chronic low density lipoprotein exposure on neutrophil function." Pulm Pharmacol Ther., Aug. 2013, vol. 26, pp. 405-411.
Qiu, et al., "The diversity of the DnaJ/Hsp40 family, the crucial partners fro Hsp70 chaperones." Cellular and Molecular Ufe Sciences, 2006, vol. 63, pp. 2560-2570.
Quark Pharmaceuticals, "In a Phase 2 Study PF-04523655 (RTP801I-14) Showed Improved Vision over Standard of Care in Patients with Diabetic Macular Edema at 12 Months." Mar. 18, 2011, 4 pgs.
Response to Office Action dated Jan. 5, 2012 for U.S. Appl. No. 12/449,265, filed Apr. 18, 2012, 22 pages.
Rincon, M. et al., "Interleukin-6, multi-drug resistance protein-1 expression and response to paclitaxel in women with metastatic breast cancer: results of cancer and leukemia group B trial 159806." Breast Cancer Research Treat, Dec. 2006, vol. 100, pp. 301-308.
Rincon, M. et al., "Prostaglandin E2 and the increase of intracellular cAMP inhibit the expression of interleukin 2 receptors in human T cells." Eur J Immunol, Nov. 1988, vol. 18, pp. 1791-1796.
Rudikoff, S. et al., "Single amino acid substitution altering antigen-binding specificity." Proc. Natl. Acad. Sci. USA, Mar. 1982, vol. 79, pp. 1979-1983.
Saibara, T. et al., "Acute hepatic failure with swollen mitochondria and microvesicular fatty degeneration of hepatocytes triggered by free radical initiator." Lab Invest., Apr. 1994, vol. 70, pp. 517-524.
Salceda, S. et al., "Hypoxia-inducible Factor 1 alpha (HIF-1a) Protein Is Rapidly Degraded by the Ubiquitin-Proteasome System under Normoxic Conditions. Its stabilization by hypoxia depends on redox-induced changes." Journal of Biological Chemistry, Sep. 5, 1997, vol. 272, pp. 22642-22647.
Saraswathi, V. et al., "Dietary Fish Oil Exerts Hypolipidemic Effects in Lean and Insulin Sensitizing Effects in Obese LDLR-1-Mice1-3", The Journal of Nutrition, Oct. 2009, pp. 2380-2386.
Saraswathi, V. et al., "Fish Oil Increases Cholesterol Storage in White Adipose Tissue with Concomitant Decrease in Inflammation, Hepatic Steatosis, and Atherosclerosis in Mice 1,2", The Journal of Nutrition, May 2007, pp. 1776-1782.

(56) References Cited

OTHER PUBLICATIONS

Scheufler, C. et al., "Structure of TPR Domain-Peptide Complexes: Critical Elements in the Assembly of the Hsp70-Hsp90 Multichaperone Machine." Cell, Apr. 14, 2000, vol. 101, pp. 199-210.
Schusdziarra et al., "Methylation-controlled J-protein MCJ acts in the import of proteins into human mitochondria." Human Molecular Genetics, vol. 22, No. 7, Apr. 1, 2013, pp. 1348-1357.
Scotto K., "Transcriptional regulation of ABC drug transporters." Oncogene, Oct. 20, 2003, vol. 22, pp. 17496-17511.
Shi et al., "Biodistribution of Small Interfering RNA at the Organ and Cellular Levels after Lipid Nanoparticle-mediated Delivery." Journal of Histochemistry & Cytochemistry 59(8), 727-740.
Shridhar, V. et al., "Loss of expression of a new member of the DNAJ protein family confers resistance to chemotherapeutic agents used in the treatment of ovarian cancer." Cancer Research, American Association for Cancer Research, vol. 61, No. 10, May 15, 2001, pp. 4258-4265.
Sladowski, D. et al., "An improved MTT assay." Journal of Immunological Methods, Jan. 4, 1993, vol. 157, pp. 203-207.
Sondermann, H. et al., "Structure of a Bag/Hsc70 Complex: Convergent Functional Evolution of Hsp70 Nucleotide Exchange Factors." Science, Feb. 23, 2001, vol. 291, pp. 1553-1557.
Sozio, MS. et al., "The role of lipid metabolism in the pathogenesis of alcoholic and nonalcoholic hepatic steatosis." Semin Liver dis. Nov. 2010, vol. 30, pp. 378-390. (Abstract only, 1 page).
Sterrenberg, J.N. et al., "Human DNAJ in cancer and stem cells." Cancer Lett, Dec. 2011, vol. 312, pp. 129-142.
Stone, R.M., et al., "Acute Myeloid Leukemia." Hematology AM. Soc. Hematol. Edu. Program, (2004), pp. 98-117.
Strathdee, G. et al., "Cell type-specific methylation of an intronic CpG island controls expression of the MCJ gene." Carcinogenesis, May 2004, vol. 25, pp. 693-701.
Strathdee. G. et al., "Demethylation of the MCJ gene in stage III/IV epithelial ovarian cancer and response to thermotherapy." Gynecologic Oncology, Jun. 2005, vol. 97, pp. 893-903.
Terada, K. et al., "A type I DnaJ homolog, DjA 1, regulates androgen receptor signaling and spermatogenesis." EMBO J, Feb. 2005, vol. 24, pp. 611-622.
Teratini et al., "A high-cholesterol diet exacerbates liver fibrosis in mice via accumulation of free cholesterol in hepatic stellate cells." Gastroenterology, Jan. 2012, vol. 142, pp. 152-164.
Torres et al., "MCJ/DnaJC15, the Mitochondrial Foe in Liver Injury." Journal of Hepatology (2016), vol. 64, No. 2, p. S236.
Treier, M. et al., "Ubiquitin-Dependent c-Jun Degradation in Vivo Is Mediated by the I:i Domain." Cell, Sep. 9, 1994, vol. 78, pp. 787-798.
Ungewickell, E. et al., "Role of auxilin in uncoating clathrin-coated vesicles." Nature, Dec. 7, 1995, vol. 378, pp. 632-635.
Vajdos, F. et al., "Comprehensive Functional Maps of the Antigen-binding Site of an Anti-ErbB2 Antibody Obtained With Shotgun Scanning Mutagenesis." Journal of Molecular Biology, Jul. 5, 2002, vol. 320, pp. 415-428.
Van Der Windt, G.J. et al., "Mitochondrial respiratory capacity is a critical regulator of COB+ T cell memory development." Immunity, Jan. 2012, vol. 36, pp. 68-78.
Vermont EPSCoR Annual State Meeting Adaptation to Climate Change in the Lake Chaplain Basin: New Understanding through Complex Systems Modeling (RACC). Aug. 5, 2014, XP055274470.
Vidal et al., "Making sense of antisense." European Journal of Cancer (2005), 41, pp. 2812-2818.

\* cited by examiner

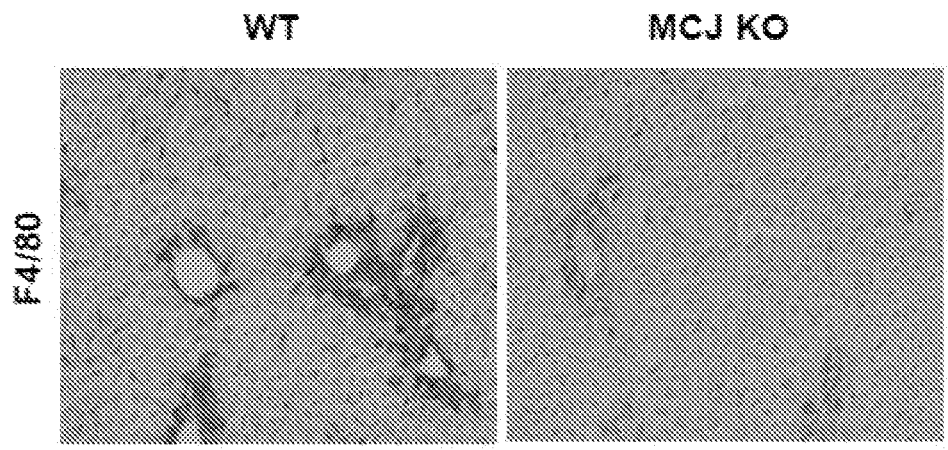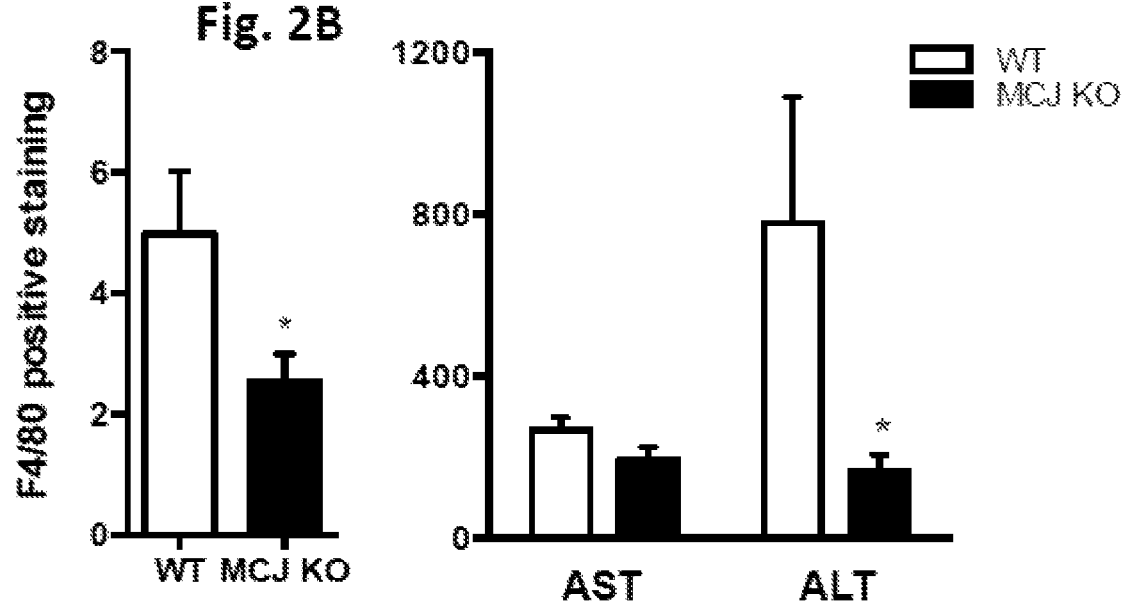

Fig. 8A
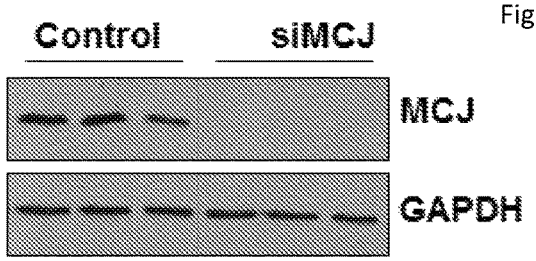
Fig. 8B
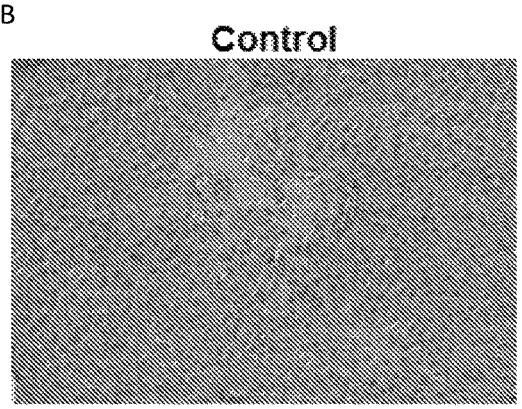
Fig. 8C
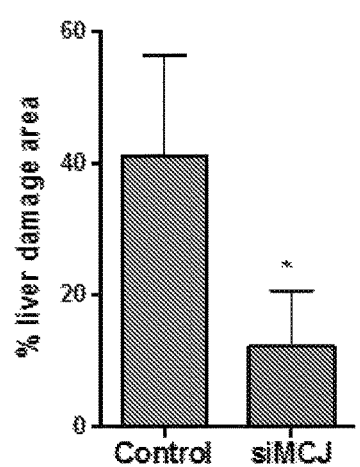
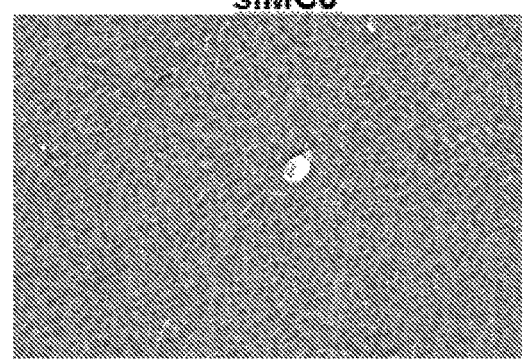

METHODS AND COMPOSITIONS TO TREAT DRUG-INDUCED DISEASES AND CONDITIONS

RELATED APPLICATIONS

This application is a National Stage Filing under U.S.C. § 371 of PCT International Application PCT/US16/41663, filed Jul. 9, 2016 which was published under PCT Article 21(2) in English, which claims benefit under 35 U.S.C. § 119(e) of U.S. Provisional application Ser. No. 62/190,803 filed Jul. 10, 2015 and U.S. Provisional application Ser. No. 62/324,584, filed Apr. 19, 2016, the disclosure of each of which is incorporated by reference herein in its entirety.

GOVERNMENT INTEREST

This invention was made with government support under R21 AI094027 awarded by the National Institutes of Health. The government has certain rights in the invention.

FIELD OF THE INVENTION

The invention relates, in part, to methods and compounds useful to treat toxicity and drug-induced diseases and conditions.

BACKGROUND

Cirrhosis is a worldwide global health problem affecting up to 1% of the population and the major risk factor for progression to hepatocellular carcinoma (HCC), one of the most frequent and deadliest solid organ tumors. Although several etiological factors contribute to the development of cirrhosis, hepatitis C, fatty liver and alcohol abuse are the most common causes. Cirrhosis is characterized by an advanced stage of liver fibrosis. Currently, although liver transplantation represents a cornerstone in the management of cirrhosis, its application is limited by stringent selection criteria, high costs and donor graft shortage.

Liver injury can also be induced by accumulation of drugs. Drug-induced liver injury (DILI) includes injury caused by medicinal herbs, plants, and nutritional supplements as well as a number of drugs. Drug-induced injury mechanisms may include covalent binding of the drug to cellular proteins resulting in immune injury, inhibition of cell pathways, blockage of cellular transport pumps, induction of apoptosis, and interference with mitochondrial function, etc. Overdoses with acetaminophen (Tylenol) leading to liver toxic effects have been reported as leading cause of acute liver failure in the US and the UK. The FDA proposed to limit the hepatotoxicity of acetaminophen by reducing its therapeutic index and minimizing the combinational therapy.

SUMMARY OF THE INVENTION

According to one aspect of the invention, methods for treating toxicity and drug-induced diseases and conditions in the liver and other organs and organ systems in a subject are provided. The methods include administering to a cell and/or subject in need of such treatment an MCJ-inhibiting compound in an amount effective to treat the toxicity and drug-induced disease or condition in the cell and/or subject, respectively.

In one aspect of the invention, methods for treating a drug-induced disease or condition in a subject are provided. The methods include administering to a subject in need of such treatment an MCJ-modulating compound in an amount effective to treat the drug-induced disease or condition in the subject. In some embodiments, the MCJ-modulating compound is an MCJ-inhibiting compound that reduces MCJ polypeptide activity in the subject. In some embodiments, decreasing the MCJ polypeptide activity comprises decreasing one or more of an MCJ polypeptide level or activity. In certain embodiments, the drug-induced disease or condition is one or more of a drug-induced liver disease or condition and kidney disease or condition, heart disease or condition, and cardiovascular disease or condition. In some embodiments, the disease or condition is an acute disease or condition. In some embodiments, the disease or condition is a chronic disease or condition. In certain embodiments, the MCJ-modulating compound comprises one or more of a MCJ molecule, an anti-MCJ polypeptide antibody or functional fragment thereof, and a small molecule MCJ inhibitor. In some embodiments, the MCJ-modulating compound further comprises a targeting agent, optionally a mitochondrial targeting agent. In some embodiments, the MCJ molecule is a variant MCJ polypeptide or a polynucleotide that encodes a variant MCJ polypeptide. In some embodiments, the small molecule MCJ inhibitor is a small interference RNA molecule (siRNA), small hairpin RNA (shRNA) molecule, an antisense DNA oligo, a small guide RNA (sgRNA) molecule, a transcription activator-like effector nuclease (talens) molecule. In certain embodiments, the siRNA molecule comprising a nucleic acid sequence set forth herein as SEQ ID NO:7. In certain embodiments, the siRNA molecule comprising a nucleic acid sequence set forth herein as SEQ ID NO: 21. In some embodiments, the MCJ-modulating compound is administered in a pharmaceutical composition, and wherein the pharmaceutical composition further comprises a pharmaceutically acceptable carrier and optionally comprises one or more of a carrier agent, a delivery agent, a labeling agent, and a targeting agent. In some embodiments, the carrier agent comprises one or more of a nanocarrier, a cell-penetrating peptide, a polymer, a dendrimer, an siRNA bioconjugate, and a lipid-based siRNA carrier. In certain embodiments, the pharmaceutical composition additionally comprises a drug known to or suspected of inducing the drug-induced disease or condition. In some embodiments, the drug-induced disease or condition comprises one or more of a drug-induced: cirrhosis, liver fibrosis, venoocclusive liver disease, idiosyncratic toxicity, Budd-Chiari syndrome, liver damage; kidney damage, drug allergy, Acute Kidney Injury (AKI), fulminant hepatitis, cholestasis, cardiotoxicity, and alcohol intake. In some embodiments, the inducing drug of the drug-induced disease or condition comprises one or more of ethanol, a pharmaceutical agent, and a biological agent. In some embodiments, the inducing drug enters the subject by an ingestion means, which optionally comprises one or more of: inhalation, injection, absorption, implantation, infusion, drinking, and eating. In certain embodiments, the pharmaceutical agent comprises a statin, an antidepressant, an antibiotic, a benzodiazepine, nicotinic acid, tacrine, aspirin, quinidine, NSAIDs (including but not limited to: aspirin, indomethacin, ibuprofen, naproxen, piroxicam, nabumetone), acetaminophen, phenytoin, isoniazid, diclofenac, Augmentin (combination of amoxicillin/clavulanic acid), minocycline, nitrofurantoin, fenofibrate, methamphetamine, amphetamine, erythromycin, chlorpromazine, Cotrimoxazole (combination of sulfamethoxazole and trimethoprim), amitriptyline, temazepam, diazepam, carbamazepine, ampicillin, rifampin, estradiol, captopril, birth control pills (oral contraceptives), an anabolic steroid, disulfiram, vitamin A, haloperidol, imipramine, tetracycline, phenytoin, methotrexate, amiodarone, methyldopa, a chemotherapeutic agent, a contrast dye, a thiazine (including but not limited to phenothiazine), chloramphenicol, digoxin, digitoxin, oxazepam, phenobarbital, quinidine, vancomycin, theophylline, verapamil, an interferon (including but not limited to interferon beta 1a), and warfarin. In certain embodiments, a biological agent is an herbal extract. In certain embodiments the herbal extract comprises one or more of: Ma Huang, Kava Kava, chaparral, valerian, horse chestnut extract, and Kava leaves. In some embodiments, the drug-induced disease or condition is not a metabolic disease or condition of overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; or cancer. In some embodiments, the subject does not have one or more of a metabolic disease or condition of overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; and cancer. In some embodiments, the MCJ-modulating compound is administered to the subject at one or more of before, concurrently with, and after ingestion by the subject of a drug suitable to induce the drug-induced disease or condition.

According to another aspect of the invention, methods of reducing a drug-induced disease or condition in a cell are provided. The methods include contacting the cell with an MCJ-inhibiting compound in an amount effective to decrease an MCJ polypeptide activity in the cell. In certain embodiments, decreasing the MCJ polypeptide activity comprises decreasing one or more of a level or function of an MCJ polypeptide in the cell. In some embodiments, the cell is in vitro, ex vivo, or in vivo. In some embodiments, the in vivo cell is in a subject and the contacting comprises administering the MCJ-inhibiting compound to the subject. In certain embodiments, the MCJ-inhibiting compound comprises a MCJ molecule, an anti-MCJ polypeptide antibody or functional fragment thereof, or a small molecule MCJ inhibitor. In some embodiments, the MCJ-inhibiting compound further comprises a targeting agent, optionally a mitochondrial targeting agent. In some embodiments, the MCJ molecule is a variant MCJ polypeptide or a polynucleotide that encodes a variant MCJ polypeptide. In certain embodiments, the small molecule MCJ inhibitor is an siRNA molecule. In some embodiments, the siRNA molecule comprising a nucleic acid sequence set forth herein as SEQ ID NO:7. In some embodiments, the small molecule MCJ-inhibitor molecule has the nucleic acid sequence set forth herein as SEQ ID NO:21. In some embodiments, the cell is contacted with the MCJ-inhibiting compound that is in a pharmaceutical composition, and wherein the pharmaceutical composition further comprises a pharmaceutically acceptable carrier and optionally comprises one or more of a carrier agent, a delivery agent, a labeling agent, and a targeting agent. In some embodiments, the drug-induced disease or condition is one or more of a drug-induced liver disease or condition and kidney disease or condition, a drug-induced cardiac disease or condition. In certain embodiments, the drug-induced disease or condition is one or more of an acute disease or condition and a chronic disease or condition. In some embodiments, the carrier agent comprises one or more of a nanocarrier, a cell-penetrating peptide, a polymer, a dendrimer, an siRNA bioconjugate, and a lipid-based siRNA carrier. In some embodiments, the pharmaceutical composition additionally comprises a drug known to or suspected of inducing the drug-induced disease or condition. In certain embodiments, the drug-induced disease or condition comprises one or more of a drug-induced: cirrhosis, liver fibrosis, veno-occlusive liver disease, idiosyncratic toxicity, Budd-Chiari syndrome, liver damage; kidney damage, drug allergy, Acute Kidney Injury (AKI), fulminant hepatitis, cholestasis, cardiotoxicity, and alcohol intake. In some embodiments, the inducing drug of the drug-induced disease or condition comprises one or more of ethanol, a pharmaceutical agent, and a biological agent. In some embodiments, the inducing drug contacts the cell, thereby inducing in the cell the drug-induced disease or condition. In certain embodiments, the pharmaceutical agent comprises statin, an antidepressant, an antibiotic, a benzodiazepine, nicotinic acid, tacrine, aspirin, quinidine, NSAIDs (including but not limited to: aspirin, indomethacin, ibuprofen, naproxen, piroxamin, nabumetone), acetaminophen, phenytoin, isoniazid, diclofenac, Augmentin (combination of amoxicillin/clavulanic acid), minocycline, nitrofurantoin, fenofibrate, methamphetamine, amphetamine, erythromycin, chlorpromazine, Cotrimoxazole (combination of sulfamethoxazole and trimethoprim), amitriptyline, temazepam, diazepam, carbamazepine, ampicillin, rifampin, estradiol, captopril, birth control pills (oral contraceptives), an anabolic steroid, disulfiram, vitamin A, haloperidol, imipramine, tetracycline, phenytoin, methotrexate, amiodarone, methyldopa, a chemotherapeutic agent, a contrast dye, a thiazine (including but not limited to phenothiazine), chloramphenicol, digoxin, digitoxin, oxazepam, phenobarbital, quinidine, vancomycin, theophylline, verapamil, an interferon (including but not limited to interferon beta 1a), and warfarin. In some embodiments, the biological agent is an herbal extract. In certain embodiments, the herbal extract comprises one or more of: Ma Huang, Kava Kava, chaparral, valerian, horse chestnut extract, and Kava leaves. In certain embodiments, the drug-induced disease or condition is not a metabolic disease or condition of overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; or cancer. In some embodiments, the cell does not have one or more of a metabolic diseases or conditions of overweight, weight gain, obesity, nonalcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; and cancer. In some embodiments, the cell is contacted with the MCJ-modulating compound at one or more of before, concurrently with, and after contacting the cell with a drug suitable to induce the drug-induced disease or condition.

According to yet another aspect of the invention, compositions that include an MCJ-inhibiting compound and a pharmaceutically acceptable carrier are provided. In certain embodiments, the composition additionally includes one or more of a carrier agent, a delivery agent, a labeling agent, and a targeting agent. In some embodiments, the carrier agent comprises one or more of a nanocarrier, a cell-penetrating peptide, a polymer, a dendrimer, an siRNA bioconjugate, and a lipid-based siRNA carrier. In some embodiments, the pharmaceutical composition additionally comprises a drug known to or suspected of inducing the drug-induced disease or condition. In certain embodiments, the MCJ-inhibiting compound comprises a targeting agent, optionally a mitochondrial targeting agent. In some embodiments, the MCJ-inhibiting compound comprises a small molecule MCJ inhibitor. In certain embodiments, the small molecule MCJ inhibitor is a small interference RNA molecule (siRNA), small hairpin RNA (shRNA) molecule, an antisense DNA oligo, a small guide RNA (sgRNA) molecule, a transcription activator-like effector nuclease (talens) molecule. In some embodiments, the small molecule MCJ-inhibitor molecule has the nucleic acid sequence set forth herein as SEQ ID NO:7. In some embodiments, the small molecule MCJ-inhibitor molecule has the nucleic acid sequence set forth herein as SEQ ID NO:21. In some embodiments, the composition additionally includes a drug suitable to induce a drug-induced disease or condition in at least one of a cell and a subject when the drug is contacted with the cell or delivered into the subject, respectively.

The present invention is not intended to be limited to a composition or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

Brief Description of the Sequences

SEQ ID NO: 1 is amino acid sequence of human DNAJ
domain-containing protein MCJ set forth as
GENBANK ® Accession No. AAD38506.1:
MAARGVIAPVGESLRYAEYLQPSAKRPDADVDQQGLVRSLIAVGLGVAAL

AFAGRYAFRIWKPLEQVITETAKKISTPSFSSYYKGGFEQKMSRREAGLI

LGVSPSAGKAKIRTAHRRVMILNHPDKGGSPYVAAKINEAKDLLETTTK

H.

SEQ ID NO: 2 is mRNA sequence (complete CDS) of
human DNAJ domain-containing protein MCJ set forth
as GENBANK ® Accession No. AF126743.1:
ggtcaggaaagctcaggcaagcccaccctcaggcattacagctagactcc gagcttactgggcagtcatctgattcgaccaacatcagttcgcagggctt aagcccagtccttacggcggctggggagggaccaggcccaagtatataa agctccctgagggtccgcgttggctttgcgcctgtgagtgtgattcaaga acgtcccagtgcccttggctcctttcggagtgtgaccccgtgcttgcacg ggacacgttacccagctcgggtgagaagggtatcttccgggaacctcgcc tttaatagcacaacgagcgcagagtccactggatctgcgagaagaaaccg cgctaactagtttgtccctacggccgcctcgtagtcactgccgcggcgcc ttgagtctccgggccgccttgccatggctgcccgtggtgtcatcgctcca gttggcgagagtttgcgctacgctgagtacttgcagccctcggccaaacg gccagacgccgacgtcgaccagcagggactggtaagaagtttgatagctg taggactgggtgttgcagctcttgcatttgcaggtcgctacgcatttcgg atctggaaacctctagaacaagttatcacagaaactgcaaagaagatttc aactcctagcttttcatcctactataaaggaggatttgaacagaaaatga gtaggcgagaagctggtcttattttaggtgtaagcccatctgctggcaag gctaagattagaacagctcataggagagtcatgattttgaatcacccaga taaaggtggatctccttacgtagcagccaaaataaatgaagcaaaagact tgctagaaacaaccaccaaacattgatgcttaaggaccacactgaaggaa aaaaaagaggggacttcgaaaaaaaaaaaagccctgcaaaatattctaa aacatggtcttcttaattttctatatggattgaccacagtcttatcttcc accattaagctgtataacaataaaatgttaatagtcttgctttttattat cttttaaagatctccttaaattct.

SEQ ID NO: 3 is amino acid sequence of a mouse
DNAJ domain-containing protein:
MATGGGVTSRESLRYAEYLPPSAQRSDADIDHTAGRRLIAVGLGVAAVAF

AGRYAFQIWKPLEQVITATARKISSPSFSSYYKGGFEQKMSKREASLILG

VSPSAGKAKIRTAHKRIMILNHPDKGGSPYVASKINEAKDLLEASSKAN.

SEQ ID NO: 4 is amino acid sequence of a human
DnaJ (Hsp40) homolog of subfamily C set forth as
GENBANK ® Accession No. AAH95400.1:
MAARGVIAPVGESLRYAEYLQPSAKRPDADVDQQRLVRSLIAVGLGVAAL

AFAGRYAFRIWKPLEQVITETAKKISTPSFSSYYKGGFEQKMSRREAGLI

LGVSPSAGKAKIRTAHRRVMILNHPDKGGSPYVAAKINEAKDLLETTTK

H.

SEQ ID NO: 5 is nucleotide sequence of human DnaJ
(HSP40) homolog of subfamily C set forth as
GENBANK ® Accession No. BC095400.1:
agtctccgggccgccttgccatggctgcccgtggtgtcatcgctccagtt ggcgagagtttgcgctacgctgagtacttgcagccctcggccaaacggcc agacgccgacgtcgaccagcagagactggtaagaagtttgatagctgtag gcctgggtgttgcagctcttgcatttgcaggtcgctacgcatttcggatc tggaaacctctagaacaagttatcacagaaactgcaaagaagatttcaac tcctagcttttcatcctactataaaggaggatttgaacagaaaatgagta

```
ggcgagaagctggtcttattttaggtgtaagcccatctgctggcaaggct
aagattagaacagctcataggagagtcatgattttgaatcacccagataa
aggtggatctccttacgtagcagccaaaataaatgaagcaaaagacttgc
tagaaacaaccaccaaacattgatgcttaaggaccacactgaaggaaaaa
aaaagaggggacttcaaaaaaaaaaaaaaagccctgcaaaatattctaaa
acatggtatataattttctatatggattgaccacagtcttatcttccacc
attaagctgtataacaataaaatgttaatagtcttgcttttattatatt
taaagatctccttaaattctataactgatctttttcttattttgtttgt
gacattcatacattttaagattttgttatgttctgaattcccccctac
acacacacacacacacacacacgtgcaaaaaatatgatcaagaa
tgcaattgggatttgtgagcaatgagtagacctcttattgtttatatttg
taccctcattgtcaattttttttttagggaatttgggactctgcctatata
aggtgttttaaatgtcttgagaacaagcactggctgatacctcttggaga
tatgatctgaaatgtaatggaatttattaaatggtgtttagtaaagtagg
ggttaaggacttgttaaagaaccccactatctctgagaccctatagccaa
agcatgaggacttggagagctactaaaatgattcaggtttacaaaatgag
ccctgtgaggaaaggttgagagaagtctgaggagtttgtatttaattata
gtcttccagtactgtatattcattcattactcattctacaaatatttatt
gaccccttttgatgtgcaaggcactatcgtgcgtcccctgagagttgcaa
gtatgaagcagtcatggatcatgaaccaaaggaacttatatgtagaggaa
ggataaatcacaaatagtgaatactgttagatacagatgatatattttaa
aagttcaaaggaagaaaagaatgtgttaaacactgcatgagaggaggaat
aagtggcatagagctaggctttagaaaagaaaaatattccgataccatat
gattggtgaggtaagtgttattctgagatgagaattagcagaaatagata
tatcaatcggagtgattagagtgcagggtttctggaaagcaaggtttgga
cagagtggtcatcaaaggccagccctgtgacttacactgcattaaattaa
tttcttagaacatagtccctgatcattatcactttactattccaaaggtg
agagaacagattcagatagagtgccagcattgtttcccagtattcccttta
caaatatgggttcattccaggtaaactgaactactgcattgtttctatct
taaaatacttttagatatcctagatgcatattcaacttctaacattctg
tagtttaggagttctcaaccttggcattattgacatgttaggccaaataa
ttttttttgtgggaggtctcttgtgcgttttagatgattagcaataatcc
ctgacctgttatctactaaagactagtcgtttctcatcagttgtgacaac
aaaaatggttccagatattgccaaatgcccttttagaggacagtaatcgcc
cccagttgagaaccatttcagtaaaactttaattactatttttctttg
gtttataaaataatgatcctgaattaaattgatggaaccttgaagtcgat
aaaatatatttatgattaaagtccccatacgtgtcctactaattttctca
tgctttagtgttttcacttttctcctgttatccttgtacctaagaatgcc
atcccaatcccagatgtccacctgccccaaagtctaggcatagctgaagg
ccaagctaaaatgtatccctcttttttctggtacatgcagcaaaagtaata
tgaattatcagattctgagagcaggcattgtatctgtatgtttggtgtta
cattggcacccaataaatatttgttgagcgaaaaaaaaaaaaaaa.
SEQ ID NO: 6 is a Human MCJ cDNA sequence.
caccctcaggcactacagctagactccgagcttactgggcagtcatctga
ttcgaccaacatcagttcgcagggcttaagcccagtcccttacggcggcc
tggggagggaccaggcccaagtatataaagctccctgagggtccgcgttg
gctttgcgcctgtgagtgtgattcaagaacgtcccagtgcccttggctcc
tttcggagtgtgacccccgtgcttgcacgggacacgttacccagctcggt
gagaagggtatcttccgggaacctcgcctttaatagcacaacgagcgcag
agtccactggatctgcgagaagaaaccgcgctaactagtttgtccctacg
gccgcctcgtagtcactgccgcggcgccttgagtctccgggccgccttgc
catggctgcccgtggtgtcatcgctccagttggcgagagtttgcgctacg
ctgagtacttgcagccctcggccaaacgccagacgccgacgtcgaccag
cagagactggtaagaagtttgatagctgtaggactgggtgttgcagctct
tgcatttgcaggtcgctacgcatttcggatctgaaacctctagaacaag
ttatcacagaaactgcaaagaagatttcaactcctagcttttcatcctac
tataaaggaggatttgaacagaaaatgagtaggcgagaagctggtcttat
tttaggtgtaagcccatctgctggcaaggctaagattagaacagctcata
ggagagtcatgattttgaatcacccagataaaggtggatctccttacgta
gcagccaaaataaatgaagcaaaagacttgctagaaacaaccaccaaaca
ttgatgcttaaggaccacactgaaggaaaaaaaaagaggggacttcgaaa
aaaaaaagccctgcaaaatattctaaaacatggtatataattttctat
atggattgaccacagtcttatcttccaccattaagctgtataacaataaa
atgttaatagtcttgattttattatatttaaagatctccttaaattctat
aactgatctttttcttattttgtttgtgacattcatacattttaagat
tttgttatgttctgaattcccccctacacacacacacacacacacacac
acacacgtgcaaaaaatatgatcaagaatgcaattgggatttgtgagc
aatgagtagacctcttattgtttatatttgtaccctcattgtcaattttt
ttttagggaatttgggactctgcctatataaggtgttttaaatgtcttga
gaacaagcactggctgatacctatggagatatgatctgaaatgtaatgga
atttattaaatggtgtttagtaaagtaggggttaaggacttgttaaagaa
ccccactatctctgagaccctatagccaaagcatgaggacttggagagct
actaaaatgattcaggtttacaaaatgagccctgtgaggaaaggttgaga
gaagtctgaggagtttgtatttaattatagtcttccagtactgtatattc
attcattactcattctacaaatatttattgaccccttttgatgtgcaagg
cactatcgtgcgtcccctgagagttgcaagtatgaagcagtcatggatca
tgaaccaaaggaacttatatgtagaggaaggataaatcacaaatagtgaa
tactgttagatacagatgatatattttaaaagttcaaaggaagaaaagaa
tgtgttaaacactgcatgagaggaggaataagtggcatagagctaggctt
tagaaaagaaaaatattccgataccatatgattggtgaggtaagtgttat
tctgagatgagaattagcagaaatagatatatcaatcggagtgattagag
```

-continued tgcagggtttctggaaagcaaggtttggacagagtggtcatcaaaggcca gccctgtgacttacactgcattaaattaatttcttagaacatagtccctg atcattatcactttactattccaaaggtgagagaacagattcagatagag tgccagcattgtttcccagtattcctttacaaatcttgggttcattccag gtaaactgaactactgcattgtttctatcttaaaatacttttagatatc ctagatgcatctttcaacttctaacattctgtagtttaggagttctcaac cttggcattattgacatgttaggccaaataattttttttgtgggaggtct cttgtgcgttttagatgattagcaataatccctgacctgttatctactaa agactagtcgtttctcatcagttgtgacaacaaaaatggttccagatatt gccaaatgccctttagaggacagtaatcgcccccagttgagaaccatttc agtaaaactttaattactatttttctttggtttataaaataatgatcc tgaattaaattgatggaaccttgaagtcgataaaatatatttcttgatta aagtccccatacgtgtcctactaattttctcatgctttagtgttttcact tttctcctgttatccttgtacctaagaatgccatcccaatcccagatgt ccacctgcccaaagtctaggcatagctgaaggccaagctaaaatgtatcc ctcttttctggtacatgcagcaaaagtaatatgaattatcagattctga gagcaggcattgtatctgtatgtttggtgttacattggcacccaataaat atttgttgagtgaatgaaaaaaaaaaaaaaaaaa.

The siRNA molecules below are also referred to as siMCJ oligos and are double stranded RNA oligos.

human siRNA sequence
SEQ ID NO: 7
gaagatttcaactcctagc.

human siRNA sequence
SEQ ID NO: 8
ggcgagaagctggtcttattt.

human siRNA sequence
SEQ ID NO: 9
gctaagattagaacagctcat.

human siRNA sequence
SEQ ID NO: 10
gctcataggagagtcatgatt.

human siRNA sequence
SEQ ID NO: 11
tttgggactctgcctatataa.

human siRNA sequence
SEQ ID NO: 12
gttgcagctcttgcatttgca.

human siRNA sequence
SEQ ID NO: 13
ctacgcatttcggatctggaa.

human siRNA sequence
SEQ ID NO: 14
gcagggactggtaagaagttt.

human siRNA sequence
SEQ ID NO: 15
gttgcagctcttgcatttgca.

human siRNA sequence
SEQ ID NO: 16
cagataaaggtggatctcctt.

human siRNA sequence
SEQ ID NO: 17
gctcataggagagtcatgatt.

human siRNA sequence
SEQ ID NO: 18
gctaagattagaacagctcat.

SEQ ID NO: 19: human siRNA sequence
gtttgatagctgtaggact.

SEQ ID NO: 20: human siRNA sequence
tcacccagataaaggtgga.

SEQ ID NO: 21: human siRNA sequence
gaagatttcaactctagat.

SEQ ID NO: 22: mouse siRNA sequence
gcgagaggctagtcttatt.

SEQ ID NO: 23 is a mouse MCJ cDNA sequence:
tcggagtcctgcagtgccatggctaccggtggcggcgtgacctccagaga ggggctgcgctacgccgaatacctgcctccttctgcccaaaggtcggacg ccgacatcgaccacacagcggggagaaggttgctagctgtaggactaggt gttgcagctgttgcatttgcaggtcgctatgcatttcagatctggaaacc tctagaacaagtaatcacggcaacagcaaggaagatttcctctccaagct tttcatcctactataaaggaggattcgagcagaaaatgagtaagcgagag gctagtcttattttaggtgtaagcccatctgctggcaaggccaagattag aacagcacacaagagaattatgattttaaaccatccagacaaaggtggat ctccttacttagcatccaaaataaatgaagcaaaagatttgctcgaagca tccagcaaagctaactgatgctaaaggactgtacataccgagggaaaatg gaacaaacgcacagctgtaaaagtccttcagaagaatgtggcacgtggtc gtgttccatactgacccagtctgttttctgtcattaagtgtgcagcaata aaagcctggcagccttgcagccttggtctggcagggacttcatccgtcaa aaaaaaaaaaaaaaaaaaaa.

BRIEF DESCRIPTION OF THE DRAWINGS

FIG. 1B is a graph showing levels of MCJ expression determined for the healthy and the cirrhosis patients. The results show a statistically significant increase in the levels of MCJ in cirrhotic livers.

FIG. 2A-B provides photomicrographic images and graphs showing use of acetaminophen administration as a mouse model for drug-induced liver injury (DILI). Results are shown for wild-type (WT) and MCJ knock-out (KO) mice that were administered acetaminophen i.p. FIG. 2A shows results after 48 hours and shows the presence of macrophages in liver sections that were examined by immunohistochemistry for F4/80 macrophage marker. FIG. 2A (left panel) shows results for WT and FIG. 2A (right panel) shows results for MCJ KO. FIG. 2B, right graph shows the levels of ALT and AST transaminase in serum. Results indicated that the KO mice were more resistant to the damage induced by acetaminophen in the liver. FIG. 2B left panel shows lower F4/80 macrophage marker in the KO mice. The MCJ KO mice developed less inflammation and had lower levels of transaminases than the WT mice. FIG. 2B (left panel) is representative of one mouse for each genotype, FIG. 2B (right panel) shows the value for n=4 mice for each genotype.

FIG. 3A shows photomicrographic images of the liver after 14 days. Tissue damage was indicated by the presence of macrophages (F4/80) by IHC as a marker of the inflammation. FIG. 3A, left panel is image from one WT one mouse and FIG. 3A, right panel is image from one MCJ KO mouse. FIG. 3B is a graph showing the F4/80 positive staining value for n=4 mice for each genotype. FIG. 3C provides a survival curve for WT and MCJ KO mice upon bile duct ligation surgery. MCJ KO mice are more resistant to develop cirrhosis-type of liver damage FIG. 4A-B provides graphs showing that MCJ shRNA (shMCJ) protected primary hepatocytes from DCA-induced death.

FIG. 5A shows MCJ expression in liver from healthy control subjects (controls) (n=7) and from patients (DILI) (n=23) with drug-induced liver injury was determined by immunohistochemistry. FIG. 5B shows expression of MCJ in liver in control mice (n=3) and in mice treated with acetaminophen (APAP) for 24 or 48 h, as determined by Western blot analysis and the ratio of MCJ relative to GAPDH as control. *, denotes statistically significant ($p<0.05$). ** denotes statistically significant ($p<0.01$).

FIG. 6A is a graph of ATP levels, FIG. 6B is a graph of mitochondrial ROS levels, and FIG. 6C is a graph showing cell death measured by TUNEL assay in WT and MCJ KO primary hepatocytes treated with acetaminophen (10 mM) for 9 h (n=3). * denotes statistically significant ($p<0.05$), *** ($p<0.001$).

FIG. 8A-C provides a blot, photomicrographic images, and a graph illustrating Administration of siMCJ prevented the acetaminophen-induced liver damage. FIG. 8A shows a blot of results from wild-type mice given an i.v. injection of siMCJ (1.7 mg/Kg) in combination with invivofectamine 3.0. (siMCJ mice) or without siMCJ (Control mice). 20 h later mice received an i.p. dose of acetaminophen (360 mg/Kg). Mice were harvested 24 h later and MCJ expression in liver was determined by Western blot analysis. Each lane of the blot represents liver from an individual mouse (n=3). FIG. 8B-C show results from mice (n=5) that were treated and harvested as described in FIG. 8A. FIG. 8B shows a representative H&E staining from a liver section and FIG. 8C shows average (n=5) of liver damage. *, $p<0.05$. Statistical significance was determined by Student's t test.

FIG. 9A shows MCJ expression in liver as determined by Western blot analysis. Each lane of the blot represents an individual mouse. FIG. 9B shows graph of ALT levels determined in serum, n=5. ** denotes statistically significant ($p<0.01$) as determined by Student's t test.

DETAILED DESCRIPTION

Figure 1A:
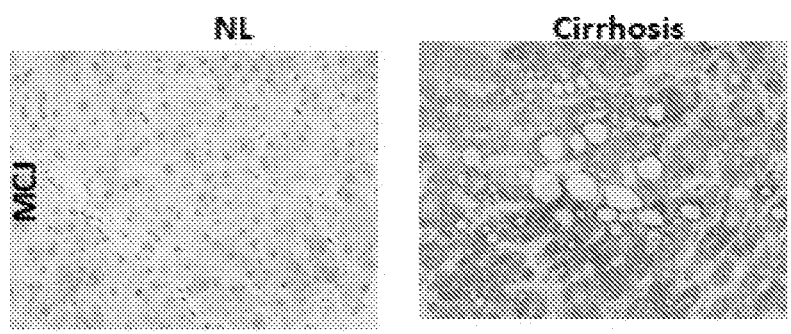
FIG. 1A-B shows photomicrographic images and a graph demonstrating increased MCJ levels in liver from cirrhosis patients. Immunohistochemistry results in FIG. 1A, left panel show MCJ expression in liver from healthy control subjects (NL) (n=5) and in FIG. 1A, right panel, show MCJ expression in liver from patients (n=16) with cirrhosis (hepatitis C).

It has now been discovered that methods and compounds that reduce MCJ polypeptide activity are useful to treat toxicity diseases and conditions. It has now been identified that by reducing activity of MCJ (DnaJC15) the effects of toxicity on cells, organs, and organ systems, can be mitigated, and that in the absence of MCJ polypeptide activity there is increased mitochondrial function in the liver. A study in a mouse model of liver cirrhosis (Bile Duct Ligation, BDL) in MCJ knockout mice have now demonstrated that MCJ deficiency protects from the development of fibrosis. Using a mouse model for drug-induced livery injury (DILI) that included administration of high doses of acetaminophen, MCJ polypeptide knockout mice were shown to be more resistant to DILI than wild-type mice. In addition, it has now been identified that treatment with siRNA for MCJ protects wild-type cells from toxic injury, for example, though not intended to be limiting, administration of siRNA for MCJ was found to protect wild-type hepatocytes from the development of toxic injury caused by acetaminophen.

Methylation-Controlled J protein (MCJ)/DnaJC15 is a member of the DnaJC subfamily of co-chaperones. MCJ is a small protein of 150 amino acids and a unique member of the DnaJC family. It contains a J-domain located at the C-terminus, as opposed to the common N-terminal position, and its N-terminal region has no homology with any other known protein. In addition, MCJ also contains a transmembrane domain while most DnaJ proteins are soluble. Phylogenetic studies have shown that MCJ is only present in vertebrates where it is highly conserved (Hatle et al., 2007). The amino acid sequence of human DNAJ domain-containing protein MCJ of GENBANK® Accession No. AAD38506.1 is set forth herein as SEQ ID NO:1. SEQ ID NO:2 is mRNA sequence of human DNAJ domain-containing protein MCJ set forth as GENBANK® Accession No. AF126743.1. GENBANK® Accession No. AAH95400.1 provides amino acid sequence of a human DnaJ (Hsp40) homolog of subfamily C, which is provided herein as SEQ ID NO:4. SEQ ID NO:5 is nucleotide sequence of human DnaJ (HSP40) homolog of subfamily C set forth as GEN-BANK® Accession No. BC095400.1. SEQ ID NO:6 is a Human MCJ cDNA sequence.

It now has been determined that the level of MCJ polypeptide activity of cells correlates with the presence or absence of a drug-induced disease or condition, and that an decreased level of MCJ polypeptide activity corresponds to an reduction in risk of a subject having a drug-induced disease or condition associated with ingestion of an inducing drug or agent. One of ordinary skill in the art will recognize that the terms such as higher, lower, decreased, reduced, increased, may represent relative levels or values as compared to control levels or values.

The invention pertains, in part, to methods of reducing activity (e.g., levels and/or function) of MCJ/DnaJC15 (also referred to herein as MCJ polypeptide) to reduce toxicity and drug-induced diseases and conditions in cells, tissues, organs, and subjects. Compositions, compounds, and methods of the invention may be used for treating a subject having, or at risk of having a drug-induced disease or condition that may be characterized by presence of a drug or agent that results in one or more of toxicity and damage to one or more of cells, tissues, organs, and organ systems in a subject. Thus, methods and compounds of the invention are useful to treat conditions in cells, tissues, and organs that are associated with drug-induced toxicity in a subject. The invention in part, also relates to decreasing/inhibiting MCJ polypeptide activity from an initial activity level in a subject to a lower activity level that is effective to reduce or eliminate symptoms of and to treat a drug-induced disease or condition.

In certain embodiments of the invention, modulating MCJ polypeptide activity includes reducing MCJ polypeptide function in a cell, tissue, and/or subject. Reducing MCJ polypeptide function may result from a decrease in the amount of MCJ polypeptide and/or from a decrease in activity of MCJ polypeptide in a cell, tissue, or subject. It will be understood that in some embodiments methods of the invention reduce the activity of an MCJ polypeptide without altering the amount of the MCJ polypeptide in a cell or tissue. A non-limiting example of a method of the invention to reduce the activity of an MCJ polypeptide includes contacting the MCJ polypeptide with an MCJ-inhibiting antibody or functional fragment thereof that binds to the MCJ polypeptide and reduces its activity. It will be understood that in some embodiments, methods of the invention reduce the amount of MCJ polypeptide in a cell or tissue, thereby reducing MCJ polypeptide activity in the cell, tissue, or subject. A non-limiting example of a method that reduces the amount of an MCJ polypeptide in a cell or tissue includes contacting the cell and/or tissue with a small molecule inhibitor, such as an RNA inhibitor of MCJ molecule, which reduces the amount of MCJ polypeptide in the cell or tissue, and concomitantly reduces the amount of MCJ polypeptide activity in the cell and/or tissue.

Treatment methods of the invention may include administering one or more MCJ-inhibiting compounds to a cell, tissue, or subject to reduce activity of an endogenous MCJ polypeptide, to reduce an amount of an endogenous MCJ polypeptide, and/or to reduce both the amount and activity of an endogenous MCJ polypeptide in the cell, tissue, and/or subject.

Molecules and compounds that inhibit an MCJ polypeptide function and/or reduce an MCJ polypeptide level are referred to herein as MCJ-modulating molecules and compounds. An MCJ-modulating molecule or compound that decreases or reduces MCJ polypeptide activity is also referred to herein as an MCJ-inhibiting molecule or compound. As used herein, the term "molecule" used in reference to an MCJ-modulating molecule refers to a variant MCJ polypeptide or fragment thereof, a small molecule MCJ inhibitor, an RNA interference molecule, an antibody or fragment thereof, an MCJ polynucleotide. As used herein, the term "compound" used in reference to an MCJ-modulating compound refers to a variant MCJ polypeptide or fragment thereof, an small molecule MCJ inhibitor, an RNA interference molecule, an antibody or fragment thereof, an MCJ polynucleotide that comprises an additional element such as a labelling agent, targeting agent, delivery agent, sequence tag, etc. Thus, in some embodiments of the invention, an MCJ-modulating compound consists of an MCJ-modulating molecule, and in certain embodiments of the invention an MCJ-modulating compound comprises an MCJ-modulating molecule and one or more additional elements.

The invention includes methods of administering an MCJ-inhibiting molecule or compound to a cell, tissue, or subject in an amount effective to decrease MCJ polypeptide activity in the cell, tissue, or subject as a treatment for a drug-induced disease or condition. As used herein, a "drug-induced disease or condition" means a disease or condition that results from ingestion by a subject of an agent (a "drug") that results in organ damage and injury to the subject. Examples of drug-induced diseases and conditions that may be treated with methods of the invention include but are not limited to a drug-induced liver disease or condition, a drug-induced kidney disease or condition, a drug-induced heart disease or condition, or a drug-induced cardiovascular disease or condition, examples of which include but are not limited to: cirrhosis, liver fibrosis, veno-occlusive liver disease, idiosyncratic toxicity, Budd-Chiari syndrome, liver damage; kidney damage, drug allergy, Acute Kidney Injury (AKI), fulminant hepatitis, cholestasis, cardiotoxicity, and alcohol intake.

Inducing Agents for Drug-Induced Diseases and Conditions

A drug-induced disease or condition results from ingestion of an agent that when present in a subject results in the drug-induced disease or condition in the subject. Examples of types of agents that when ingested may result in a drug-induced disease or condition include, but are not limited to ethanol, a pharmaceutical agent, and a biological agent (non-limiting examples of which are herbal extracts, herbal teas, herbal supplements, etc. A means of entry into a subject of an agent that induces a drug-induced disease or condition may vary. An agent that results in a drug-induced disease or condition may be administered to a subject under various circumstances, non-limiting examples of which are administration to a subject as part of a clinical treatment determined at least in part by a medical professional; as part of a treatment determined by the subject; and as part of a treatment determined by the subject in conjunction with a medical professional. An agent that results in a drug-induced disease or condition as set forth herein may be administered by a medical professional or may be administered by a subject.

In some embodiments of the invention, a pharmaceutical or biological agent may be administered to a subject to prevent or treat a clinical condition or disease and the agent may secondarily induce a drug-induced disease or condition. In such instances, the pharmaceutical agent or biological agent may be administered to a subject for imaging, to treat a condition, or for another physiological reason, and the agent administered also results in a side effect in the subject that is a drug-induced disease or condition induced by the agent. For example, although not intended to be limiting, acetaminophen may be administered to a subject to reduce post-surgical pain and may be effective to reduce the pain, but the acetaminophen may also induce a drug-induced disease or condition as set forth herein such as acetaminophen-induced liver damage, liver failure, etc.

As used herein, a "dose" used in reference to an inducing agent means the amount of the agent per subject body weight (for example, in mg/kg and the like). A dose of an inducing agent may be expressed as a single administration value or as a cumulative value of the amount of agent per subject body weight over two or more administrations of the agent to the subject. A dose of an inducing agent administered to a subject may be determined using routine procedures that may take into account factors such as subject age, weight, timing, agent clearance, and additional conditions, etc. In certain aspects of the invention, a drug-induced disease or condition may result from administration to a subject of a dose that is at or above a threshold dose of the pharmaceutical agent and/or biological agent that induces the drug-induced disease or condition. A threshold dose of an inducing agent may be a predetermined amount of the agent per subject body weight (for example, mg/kg) administered to a subject that is the dose at or above which the drug-induced disease or condition is induced by the agent. A threshold dose of an inducing agent may refer to a single or cumulative amount of the agent that induces a drug-induced disease or condition. For example, though not intended to be limiting, a pharmaceutical and/or biological agent may result in a drug-induced disease or condition when administered to a subject at or above the threshold dose for the agent, and not result in the drug-induced disease or condition when administered to the subject a dose below the threshold level. In some embodiments of the invention a threshold dose of an agent may be essentially the same in 2, 3, 4, 5, 6, or more subjects; may be essentially the same in a majority of subjects, or in all subjects.

In certain aspects of the invention, a drug-induced disease or condition may result from administration or ingestion of an agent that results in an idiosyncratic response in a subject. In certain embodiments of the invention, an idiosyncratic response may be the result of one or more specific physiological, medical, genetic, and/or other characteristics of an individual subject that result in an administered pharmaceutical or biological agent inducing a drug-induced disease or condition in that subject, but not in a subject who lacks the characteristic. For example, though not intended to be limiting, a dose of contrast dye may result in a drug-induced disease or condition when administered to one subject but the same relative dose administered to a second subject, or plurality of subjects does not result in the drug-induced disease or condition in the second subject or plurality of subjects. In another non-limiting example, a dose of an herbal extract such as Ma Huang or Kava Kava may be may be ingested by a first subject (or a plurality of subjects) without resulting in a drug-induced disease or condition as set forth herein in that subject or plurality of subjects, but an equivalent dose per subject body weight of the same herbal extract ingested by a second subject may result in a drug-induced disease or condition in the second subject. In some aspects of the invention, a drug-induced disease or condition set forth herein results from one or more of an idiosyncratic or immunoallergic pathogenesis in the subject who has ingested or has been administered a pharmaceutical agent and/or biological agent that induces the drug-induced disease or condition. In some embodiments of the invention, administration of a pharmaceutical or biological agent to a subject may result in an idiosyncratic or immunoallergic pathogenesis induced in the subject because of a physiological condition present in the subject that is not the basis for administering the pharmaceutical or biological agent to the subject, and that may absent in a plurality, most, or all other subjects.

A delivery means by which an agent that induces a drug-induced disease or condition such as those described herein may enter a subject includes ingestion, which as defined herein includes entry by means such as: inhalation, injection, absorption, implantation, infusion, oral intake, drinking, eating, etc. Non-limiting examples of delivery by absorption include, but are not limited to: transdermal absorption, absorption across a mucus membrane, absorption through a break in the skin or membrane, absorption into the eye, etc.

Numerous agents that when present in a subject may result in a drug-induced disease or condition that can be treated by method and/or compound that reduces MCJ polypeptide activity. Non-limiting examples of pharmaceutical agents that when present in a subject may result in a drug-induced disease or condition include: a statin, an antidepressant, an antibiotic, a benzodiazepine, nicotinic acid, tacrine, aspirin, quinidine, NSAIDs (including but not limited to: aspirin, indomethacin, ibuprofen, naproxen, piroxicam, nabumetone), acetaminophen, phenytoin, isoniazid, diclofenac, Augmentin (combination of amoxicillin/clavulanic acid), minocycline, nitrofurantoin, fenofibrate, methamphetamine, amphetamine, erythromycin, chlorpromazine, Cotrimoxazole (combination of sulfamethoxazole and trimethoprim), amitriptyline, temazepam, diazepam, carbamazepine, ampicillin, rifampin, estradiol, captopril, birth control pills (oral contraceptives), an anabolic steroid, disulfiram, vitamin A, haloperidol, imipramine, tetracycline, phenytoin, methotrexate, amiodarone, methyldopa, a chemotherapeutic agent, a contrast dye, a thiazine (including but not limited to phenothiazine), chloramphenicol, digoxin, digitoxin, oxazepam, phenobarbital, quinidine, vancomycin, theophylline, verapamil, an interferon (including but not limited to interferon beta 1a), and warfarin.

Non-limiting examples of biological agents that when present in a subject may result in a drug-induced disease or condition include herbal agents and extracts. Examples of herbal extracts that may result in a drug-induced disease or condition as set forth herein include but are not limited to: Ma Huang, Kava Kava, chaparral, valerian, horse chestnut extract, Kava extract, and Kava leaves.

The presence in a subject of a drug-induced diseases and conditions resulting from ingestion of a pharmaceutical agent, and/or a biological agent can be identified using routine diagnostic methods such as blood tests, scans, urine tests, etc. that are used in the art to assess organ function in subjects.

Subjects and Controls

In some aspects of the invention a subject is a human or vertebrate mammal including but not limited to a dog, cat, horse, cow, goat, and primate, e.g., monkey. Thus, the invention can be used to treat diseases or conditions in human and non-human subjects. In some aspects of the invention a subject may be a farm animal, a zoo animal, a domesticated animal or non-domesticated animal and methods of the invention can be used in veterinary prevention and treatment regimens. In some embodiments of the invention, the subject is a human and methods of the invention can be used in human prevention and treatment regimens.

Non-limiting examples of subjects to which the present invention can be applied are subjects who are diagnosed with, suspected of having, or at risk of having, a drug-induced disease or condition. Methods of the invention may be applied to a subject who, at the time of treatment, has been diagnosed as having a drug-induced disease or condition, or a subject who is considered to be at risk for having or developing a drug-induced disease or condition. In some aspects of the invention a drug-induced disease or condition is an acute drug-induced disease or condition, and in certain aspects of the invention a drug-induced disease or condition is a chronic drug-induced disease or condition.

In some embodiments of the invention, a subject does not have one or more of the following metabolic diseases or conditions: overweight, weight gain, obesity, non-alcoholic fatty liver disease, diabetes, insulin-resistance, alcoholic fatty liver disease, dyslipidemia, steatosis (e.g., metabolic-based liver steatosis, heart steatosis, kidney steatosis, muscle steatosis), abeta-lipoproteinemia, glycogen storage disease, Weber-Christian disease, lipodystrophy; metabolic liver diseases such as liver inflammation, hepatitis, steatohepatitis, Hepatitis C, Genotype 3 Hepatitis C, Alpha 1-antitrypsin deficiency, acute fatty liver of pregnancy, and Wilson disease; a metabolic kidney disease; a metabolic heart disease such as hypertension, ischemia, heart failure, cardiomyopathy; poisoning; HIV; metabolic neurodegenerative diseases: such as Parkinson's disease, Alzheimer's disease; physical exercise; and cancer.

In some embodiments of the invention, a subject may have, or have had, one or more of the following metabolic diseases or conditions: overweight, weight gain, obesity, non-alcoholic fatty liver disease, diabetes, insulin-resistance, alcoholic fatty liver disease, dyslipidemia, steatosis (e.g., metabolic-based liver steatosis, heart steatosis, kidney steatosis, muscle steatosis), abeta-lipoproteinemia, glycogen storage disease, Weber-Christian disease, lipodystrophy; metabolic liver diseases such as liver inflammation, hepatitis, steatohepatitis, Hepatitis C, Genotype 3 Hepatitis C, Alpha 1-antitrypsin deficiency, acute fatty liver of pregnancy, and Wilson disease; a metabolic kidney disease; a metabolic heart disease such as hypertension, ischemia, heart failure, cardiomyopathy; poisoning; HIV; metabolic neurodegenerative diseases: such as Parkinson's disease, Alzheimer's disease; physical exercise; and cancer.

MCJ polypeptide activity (e.g., level of MCJ polypeptide and/or function of MCJ polypeptide) can be determined and compared to control values of MCJ polypeptide activity according to the invention. A control may be a predetermined value, which can take a variety of forms. It can be a single cut-off value, such as a median or mean. It can be established based upon comparative groups, such as in groups having normal levels of MCJ polypeptide activity and groups having reduced levels of MCJ polypeptide activity. Another example of comparative groups may be groups having one or more symptoms of or a diagnosis of a drug-induced disease or condition and groups without having one or more symptoms of or a diagnosis of a drug-induced disease or condition. Typically, a control may be based on apparently healthy normal individuals in an appropriate age bracket or apparently healthy cells.

It will be understood that controls according to the invention may be, in addition to predetermined values, samples of materials tested in parallel with the experimental materials. Examples include samples from control populations or control samples generated through manufacture to be tested in parallel with the experimental samples.

In some aspects of the invention, values of MCJ polypeptide activity determined for a subject may serve as control values for later determinations of MCJ polypeptide activity in that same subject, thus permitting assessment of changes from a "baseline" MCJ polypeptide activity in a subject. Thus, an initial MCJ polypeptide activity level may be present and/or determined in a subject and methods and compounds of the invention may be used to decrease the level of MCJ polypeptide activity in the subject, with the initial level serving as a control level for that subject. Using methods and compounds of the invention, the MCJ polypeptide activity in the subject may be decreased by at least 0.5%, 1%, 5%, 10%, 20%, 30%, 40%, 50%, 60%, 70%, 80%, 90% or more compared to the initial level as a treatment for a drug-induced disease or condition in the subject.

Treatment

In certain aspects of the invention, a subject may be administered an MCJ-inhibiting compound at a time that is one or more of before, in conjunction with, and after the subject ingests an agent that induces a drug-induced disease or condition. For example, if a subject is to undergo a clinical treatment that includes at least administration of one or more pharmaceutical agents and/or biological agents known to have the potential to, or suspected of having the potential to result in a drug-induced disease or condition, the subject may be pre-treated with administration of an MCJ-modulating compound that inhibits MCJ activity in cells of the subject. In some embodiments of the invention, a subject may be administered an MCJ-inhibiting compound in combination with an agent known to have the potential to, or suspected of having the potential to result in a drug-induced disease or condition. Under certain circumstances, a subject may be administered an MCJ-inhibiting compound after the subject is identified as having or is suspected of having ingested an agent know to have potential to, or suspected of having the potential to induce a drug-induced disease or condition.

In some aspects of the invention, a subject is at risk of having or developing a drug-induced disease or condition. A subject at risk of developing a drug-induced disease or condition is one who has an increased probability of developing the drug-induced disease or condition, compared to a control risk of developing the drug-induced disease or condition. In some embodiments of the invention, a level of risk may be statistically significant compared to a control level of risk. A subject at risk may include, for instance, a subject who is, will be, or has been treated with a dose of a pharmaceutical agent known or suspect to have potential to result in a drug-induced disease or condition; a subject who has ingested a biological agent known or suspected to have potential to result in a drug-induced disease or condition; a subject who has a preexisting disease and/or a genetic abnormality that makes the subject more susceptible to a drug-induced disease or condition than a control subject without the preexisting disease or genetic abnormality; a subject having a family and/or personal medical history of a drug-induced disease or condition; a subject suspected of having ingested an agent such as a pharmaceutical agent, biological agent, known to be an agent that can induce a drug-induced disease or condition; and a subject who has previously been treated for the drug-induced disease or condition. It will be understood that a preexisting disease and/or a genetic abnormality that makes the subject more susceptible to a drug-induced disease or condition, may be a disease or genetic abnormality that when present has been previously identified as having a correlative relation to a higher likelihood of developing a drug-induced disease or condition. In certain aspects of the invention, a drug-induced disease or condition as described herein may have one or more of an idiosyncratic or immunoallergic pathogenic basis.

As used herein, the terms "treat", "treated", or "treating" when used with respect to a drug-induced disease or condition may refer to a prophylactic treatment that decreases the likelihood of a subject developing the drug-induced disease or condition, and also may refer to a treatment after the subject has developed the drug-induced disease or condition in order to eliminate or reduce the level of the drug-induced disease or condition, prevent the drug-induced disease or condition from becoming more advanced (e.g., more severe), and/or slow the progression of the drug-induced disease or condition in a subject compared to the subject in the absence of the therapy to reduce MCJ activity.

The invention in some aspects relates to methods for modulating MCJ polypeptide activity in a cell, tissue, and/or subject. As used herein the term "modulating" means changing a level of an MCJ polypeptide activity (e.g., MCJ polypeptide level and/or function) in a cell. In some embodiments of the invention, changing MCJ polypeptide activity includes changing a level of an MCJ polypeptide in a cell or tissue. Thus, decreasing activity of MCJ polypeptide in a cell may include decreasing the level (e.g., amount) of the MCJ polypeptide in the cell. Thus, some embodiments of the invention include methods of administering an MCJ-inhibiting compound to a cell, tissue or subject in an amount effective to decrease MCJ polypeptide activity in the cell, tissue, or subject as a treatment for the drug-induced disease or condition. Drug-induced diseases and conditions such as cirrhosis, liver fibrosis, veno-occlusive liver disease, idiosyncratic toxicity, Budd-Chiari syndrome, liver damage; kidney damage, drug allergy, Acute Kidney Injury (AKI), fulminant hepatitis, cholestasis, cardiotoxicity, and alcohol intake may be treated by administering an MCJ-inhibiting agent thereby decreasing MCJ-polypeptide activity in a cell, tissue, or subject, to treat the subject.

Various MCJ-modulating compounds may be used in methods of the invention, including MCJ-inhibiting compounds. Examples of MCJ-inhibiting compounds that reduce MCJ polypeptide amounts and/or activity include an MCJ molecule, which in some aspect of the invention may be a variant MCJ or a polynucleotide that encodes a variant MCJ polypeptide; an anti-MCJ polypeptide antibody or functional fragment thereof, and a small molecule MCJ inhibitor. In certain aspects of the invention, a compound useful to treat a drug-induced disease or condition is an MCJ polypeptide or a polynucleotide that encodes a variant MCJ polypeptide that interferes with, thereby reducing, the activity of a wild-type, endogenous MCJ polypeptide. In some aspects the invention a compound useful to treat a drug-induced disease or condition includes an antibody or functional fragment thereof that binds to an MCJ polypeptide or other cellular component and reduces the activity and function of an MCJ polypeptide. In some aspects of the invention, a small molecule MCJ inhibitor is a small interference RNA (siRNA) molecule, small hairpin RNA (shRNA) molecule, antisense DNA oligo, small guide RNA (sgRNA) molecule, or a transcription activator-like effector nuclease (TALENS) molecule. siRNA molecules for MCJ are also referred to herein as siMCJ oligos. A siRNA is a double-strand RNA oligonucleotide (oligo) with 2 nucleotide 3' end overhangs that activate RNAi, leading to the degradation of mRNAs in a sequence-specific manner dependent upon complimentary binding of the target mRNA. It will be understood that siRNA molecules are double-stranded RNA oligos, and as per standard practice in the art, the siRNA sequences included herein are presented showing one strand. A short hairpin RNA (shRNA) contains a loop structure and when delivered into a cell (for example, though not intended to be limiting as part of a plasmid), is processed to siRNA in the cell, which leads to the degradation of mRNAs in a sequence-specific manner dependent upon complimentary binding of the target mRNA. Methods of designing and using RNA interference molecules are known in the art, see for example: J. K. Joung & J. D. Sander 2013 *Nature Reviews Molecular Cell Biology* 14, 49-55; Ma, Y. et al., 2014 *FEBS J. December;* 281(23):5186-93; Peng, J. et al., *FEBS J.* 2015 Mar. 3. doi: 10.1111/febs.13251; Niguita, G., et al., 2015 *Front Bioeng Biotechnol.* March 25, Vol 3, Article 37. doi: 10.3389/fbioe.2015.00037; and Lagana, A. *Methods Mol Biol* 2015; 1269:393-412; *Methods Mol Biol* 2014; 1097:477-90. doi: 10.1007/978-1-62703-709-9_22; *Adv Drug Deliv Rev* 2015 Feb. 7. pii: S0169-409X(15) 00009-5. doi: 10.1016/j.addr.2015.01.007; and *Methods Mol Biol.* 2015; 1218:1-15. doi: 10.1007/978-1-4939-1538-5_1.

Non-limiting examples of a polynucleotide sequence that can be used in RNA interference methods of the invention are set forth herein as SEQ ID NO:7 and SEQ ID NO: 21. Additional sequences useful in some embodiments of RNA interference methods of the invention are also provided and set forth herein as SEQ ID NOs:8-20, and 22. Additional sequences useful in RNA interference methods of the invention may be prepared using design criteria to identify sequences that inhibit human MCJ expression. Non-limiting examples of one or more design criteria that may be used to prepare sequences for use in RNA interference methods of the invention are (1) the sequence is unique for the gene of interest (which may be identified using a BLAST search); (2) the sequence is more than 100 bp from a translation start or end; (3) the sequence has not more than three adenines or thymidines in a row; (4) the GC content of the sequence is greater than 30%; and (5) the ~19 nt target sequence may be flanked in the mRNA with AA at 5' end and in some instances, also with TT at the 3' end. Additional criteria to identify a target sequence and suitable sequences for use in RNA interference methods of the invention are routinely used in the art.

In some embodiments, methods of the invention may include directly decreasing the level of an MCJ polypeptide in a cell, tissue, or subject, for example, by delivering the MCJ inhibiting compound into the cell, tissue or subject, to treat a drug-induced disease or condition. To treat a drug-induced disease or condition in a subject, one or more cells may be contacted with an MCJ-inhibiting compound, which results in a decreased level of activity of an MCJ polypeptide in the cell. If the cell to be contacted with an MCJ-inhibiting compound is in a subject, the MCJ-inhibiting compound can be administered to the subject. Cells in which MCJ activity may be reduced using methods and MCJ-inhibiting compounds of the invention, include, but are not limited to, liver cells, kidney cells, cardiac cells, and circulatory cells.

MCJ-Inhibiting Molecules and Compounds

MCJ-inhibiting compounds of the invention may be administered to a subject in an amount and manner effective to reduce MCJ polypeptide amount and/or activity in the subject to treat a drug-induced disease or condition. Methods of the invention, in some embodiments, include administering one or more MCJ-inhibiting compounds a subject in need of such treatment to reduce a drug-induced disease or condition in the subject. MCJ-inhibiting compounds of the invention can be administered to reduce MCJ polypeptide activity in liver, kidney, cardiac tissue, or other cells, tissues, and organs of a subject.

As used herein, the terms "protein" and "polypeptide" are used interchangeably and thus the term polypeptide may be used to refer to a full-length protein and may also be used to refer to a fragment of a full-length protein. As used herein with respect to polypeptides, proteins, or fragments thereof, and polynucleotides that encode such polypeptides the term "exogenous" means the compound is administered to a cell or subject and was not an "endogenous" molecule that was naturally present in the cell or subject. It will be understood that an exogenous MCJ polypeptide or MCJ polypeptide-encoding polynucleotide may be identical to an endogenous MCJ polypeptide or MCJ polypeptide-encoding nucleic acid, respectively, in terms of its sequence, but was administered to the cell or subject.

According to some aspects of the invention, full-length MCJ polypeptides or fragments of full-length MCJ polypeptides may be administered in methods of the invention. Such MCJ polypeptides and fragments may be variant MCJ polypeptides and in some aspects of the invention, are reduced-function MCJ polypeptides that have a reduced or zero amount activity compared to normal (e.g., control) MCJ polypeptide activity. Such variant MCJ polypeptides when introduced into a cell may compete with endogenous MCJ, for example for targets, thus reducing the activity of the endogenous MCJ polypeptide. Variant polypeptides and fragments thereof may be natural fragments or may be synthesized using art-known methods, and tested for function using art-known methods. For example see methods set forth in International Patent Application No.: PCT/US2013/049885 and U.S. Pat. No. 8,354,237, the content of each of which is incorporated herein by reference. Full-length variant MCJ polypeptides and fragments thereof that are useful in methods and compositions of the invention may be recombinant polypeptides.

A "variant" wild-type or mutant full-length MCJ polypeptide or a fragment thereof that is useful in methods of the invention, may include deletions, point mutations, truncations, amino acid substitutions and/or additions of amino acids or non-amino acid moieties. Modifications of a polypeptide of the invention may be made by modification of the nucleic acid sequence that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence.

A fragment of a full-length wild-type or variant MCJ polypeptide may comprise at least up to n−1 contiguous amino acids of the full-length MCJ polypeptide having a consecutive sequence found in an MCJ polypeptide or in variant thereof (with "n" equal to the number of amino acids in the full-length MCJ polypeptide). Thus, for example, a fragment of a 150 amino acid-long MCJ polypeptide would be at least 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 149 (including each integer in between) contiguous amino acids of the 150 amino acid MCJ polypeptide.

In general, a variant MCJ polypeptide may include a polypeptide that has been modified specifically to alter a feature of the polypeptide related to its physiological activity. MCJ polypeptides can be synthesized with modifications and/or modifications can be made in an MCJ polypeptide by selecting and introducing an amino acid substitution, deletion, or addition. Modified polypeptides then can be tested for one or more activities (e.g., reducing MCJ-polypeptide activity in a cell or subject and efficacy as a treatment of a drug-induced disease or condition, etc.) to determine which modification provides variant polypeptide with desired properties.

In some embodiments of the invention, a level or function of a MCJ polypeptide may be reduced by genetically introducing an MCJ-inhibiting compound into a cell. Targeting agents and methods may be used to aid in delivery of an MCJ-inhibiting compound to a specific cell type, cell subtype, organs, spatial regions within a subject, and/or to sub-cellular regions within a cell. Art-known methods such as genetic targeting may also be used in embodiments of the invention to control of the amount of an MCJ-inhibiting compound in a cell and/or subject. Some embodiments of the invention may include a reagent for genetically targeted expression of an MCJ-inhibiting molecule, for example a variant MCJ polypeptide, wherein the reagent comprises a vector that contains a nucleic acid that encodes the variant MCJ polypeptide or a fragment thereof.

Certain aspects of the invention include methods of administering antibodies or antigen-binding fragments thereof that specifically bind to an MCJ polypeptide and reduce MCJ polypeptide activity. Such antibodies or antigen-binding fragments thereof may be administered to a cell and/or subject to inhibit MCJ polypeptide activity in the cell and/or subject. The term "antigen-binding fragment" of an antibody as used herein, refers to one or more portions of an antibody that retain the ability to specifically bind to an antigen (e.g., an MCJ polypeptide) and reduce the antigen's activity. One may prepare and test an antigen-binding fragment of an MCJ-activity-inhibiting antibody for use in methods of the invention using art-known methods and routine procedures. In some embodiments of the invention, antibodies are recombinant antibodies, polyclonal antibodies, monoclonal antibodies, humanized antibodies or chimeric antibodies, or a mixture of these. Examples of antibodies known to specifically bind the MCJ polypeptide include, but are not limited to monoclonal antibodies i) WN.F3, generated from hybridoma N-MCJ 3C1.3F3, which was deposited under ATCC no. # PTA-8135; ii) WN.A12, generated from hybridoma cell line N-MCJ 3C1.5A12, which was deposited under ATCC no. # PTA-8133; and iii) WN.E4 generated from hybridoma cell line N-MCJ 2A2.5E4, which was deposited under. ATCC no. # PTA-8134 (see U.S. Pat. No. 8,354,237, the content of which is incorporated herein by reference). The WN.F3, WN.A12, and WN.E4 antibodies are examples of antibodies that may be used in methods of the invention as MCJ-modulating compounds. Additional antibodies for use in methods of the invention may be produced and tested using art-known methods in conjunction with the disclosure herein and in the disclosure set forth in U.S. Pat. No. 8,354,237, and see also, Hatle et al. *Mol Cell Biol.* 2007 April; 27(8):2952-66, the content of each of which is incorporated herein by reference.

Additional MCJ-modulating compounds that may be administered in treatment methods of the invention include small molecules or chemicals that inhibit MCJ polypeptide activity. Examples provided herein, though not intended to be limiting are RNA interference (RNAi) molecules. RNAi molecules may be administered to cells, tissues and subjects to inhibit gene expression. In RNA interference methods, RNAs may be administered to a cell and/or subject and the RNA molecules bind to other specific mRNA molecules and decrease their activity, thereby reducing the translation of the mRNA to protein. In some embodiments of the invention, RNAi methods are used to reduce expression of an MCJ polypeptide in a cell, tissue, and/or subject. Thus, methods of the invention may include administrating of one or more RNAi molecules to a cell and/or subject in an amount effective to reduce MCJ polypeptide expression thereby reducing MCJ polypeptide activity in the cell and/or subject. Methods of identifying and testing such small molecules, for example RNA interference molecules, may include use of art-known library screening and testing procedures in conjunction with the teaching provided herein. Examples of types of RNAi molecules that can be used in methods of the invention to inhibit MCJ polypeptide activity include, but are not limited to small interfering RNA (siRNA), small hairpin RNA (shRNA), antisense DNA oligo, small guide RNA (sgRNA), and transcription activator-like effector nucleases (talens). Methods of designing and using RNAi molecules are known in the art, see for example: J. K. Joung & J. D. Sander 2013 *Nature Reviews Molecular Cell Biology* 14, 49-55; Ma, Y. et al., 2014 *FEBS J.* December; 281(23):5186-93; Peng, J. et al., *FEBS J.* 2015 Mar. 3. doi: 10.1111/febs.13251; Niguita, G., et al., 2015 *Front Bioeng Biotechnol.* March 25, Vol 3, Article 37. doi: 10.3389/fbioe.2015.00037; Lagana, A. *Methods Mol Biol.* 2015; 1269:393-412; *Methods Mol Biol* 2014; 1097:477-90. doi: 10.1007/978-1-62703-709-9_22; *Adv Drug Deliv Rev* 2015 Feb. 7. pii: 50169-409X(15)00009-5. doi: 10.1016/j.addr.2015.01.007; and *Methods Mol Biol.* 2015; 1218:1-15. doi: 10.1007/978-1-4939-1538-5_1.

MCJ polypeptide modulating compounds of the invention may be administered singly or in combination with one or more additional compounds. An MCJ-inhibiting compound administered to a subject or cell to treat a drug-induced disease or condition may act in a synergistic manner with one or more other therapeutic agents or treatments and increase the effectiveness of the one or more therapeutic agents or activities and/or to increase the effectiveness of the MCJ-inhibiting compound in treating the drug-induced disease or condition.

Treatment methods of the invention that include administration of a MCJ-inhibiting compound can be used prior to the onset of a drug-induced disease or condition and/or when the drug-induced disease or condition is present, including at an early stage, mid-stage, and late stage of the drug-induced disease or condition and all times before and after any of these stages. Methods of the invention may also be to treat subjects who have previously been treated for a drug-induced disease or condition with one or more other medicaments that were not successful, were minimally successful, and/or are no longer successful at treating the drug-induced disease or condition in the subject.

It will be understood that additional MCJ-modulating compounds can be identified and used in methods of the invention. For example, candidate compounds can be can be tested for their ability to decrease MCJ polypeptide activity (level and/or function) and their ability to treat a drug-induced disease or condition using assays and methods presented herein.

Components of MCJ-Inhibiting Compounds

MCJ-modulating compounds of the invention (such as compounds comprising a variant MCJ molecule, an anti-MCJ polypeptide antibody or functional fragment thereof, a small molecule MCJ inhibitor, etc.) described herein can be administered alone or in conjugation with other components such as targeting agents, labeling agents, membrane-crossing delivery agents, etc. in treatment methods of the invention. Thus, in some embodiments of the invention an MCJ-inhibiting compound includes an MCJ-inhibiting molecule and optionally one or more additional components.

Targeting agents useful according to some embodiments of methods of the invention may, include agents that direct an MCJ-inhibiting compound of the invention to and/or into a cell to be treated such as a liver cell, cardiac cell, circulatory cell, kidney cell, hepatocyte, etc. A targeting compound of choice will depend upon the nature of the drug-induced disease or condition. In a non-limiting example, in some embodiments it may be desirable to target an MCJ-inhibiting compound to and/or into a liver cell, or a kidney cell, etc. It will be understood that in some embodiments of methods of the invention, an MCJ-inhibiting compound includes just the MCJ-inhibitor molecule, without any additional attached molecules. For example, in some aspects of the invention an RNAi molecule may be administered to a cell and/or subject in a "naked" form, meaning no delivery molecules, labels, etc. attached to the RNAi molecule.

In cases where an MCJ-inhibiting molecule is attached to or in a composition with one or more: cell or tissue-carrier agent, targeting agent, labeling agent, delivery agent, etc. a skilled artisan will be aware of and able to select and use suitable agents for use in methods of the invention. In some aspects of the invention, a carrier agent comprises one or more of a nanocarrier, a cell-penetrating peptide, a polymer, a dendrimer, an siRNA bioconjugate, and a lipid-based siRNA carrier.

In some aspects of the invention, a targeting agent may be a mitochondrial targeting agent, which is part of an MCJ-inhibiting compound administered in methods of the invention. Delivery agents for RNAi molecules are well known in the art and include, but are not limited to aptamers; galactosamine; NAcGalactosamine; PEG; cholesterol; lipids; cell-penetrating peptides, including but not limited to cationic cell-penetrating peptides; nanocarriers, etc. Targeting agents that may be used to deliver MCJ-inhibitor molecules and compounds of the invention to mitochondria include, but are not limited to: Gramicidin S based mitochondrial targeting agents, agents utilizing the carnitine-acylcarnitine translocase system, cytochromes, malate dehydrogenase. Examples of targeting agents that may be used in some embodiments of the invention are set forth in Diekert, K., et al., *PNAS* (1999) vol 96, No. 21, 11752-11757; Addya, S., et al., *J. Cell Biology*, (1997) Vol. 139, No. 3, 589-599; Del Gaizo, V., et al., (2003) *Mol. Gen. and Metabol.* Vol. 80, 170-180, the content of each of which is incorporated herein by reference. Additional art known delivery and targeting means and procedures are described in *Ther Deliv.* 2015 April; 6(4):491-507. doi: 10.4155/tde.15.2, which discloses cationic cell-penetrating peptides as vehicles; *Int J Mol Sci.* 2015 Mar. 6; 16(3):5254-70. doi: 10.3390/ijms1603525, which describes various delivery methods, such as use of naked siRNA for inhalation delivery; Nanomedicine (Loud). 2015 April; 10(7):1165-88. doi: 10.2217/nnm.14.214, which discloses methods and materials for use of nanoparticles as a delivery system for siRNA; *Methods Mol Biol.* 2015; 1218:201-16. doi: 10.1007/978-1-4939-1538-5_12, which discloses methods of targeting to selected cells (such as use of conjugation to a peptide, an antibody etc); *Bioengineered.* 2014 May-June; 5(3):152-4. doi: 10.4161/bioe.28062. Epub 2014 Feb. 3, which describes the use of copolymers (also referred to as plyplexes) for delivery; *Curr Pharm Biotechnol.* 2014; 15(7):659-72, which describes use of liposomes, nanoparticles, and lipid nanoparticles for delivery; and *Adv Drug Deliv Rev.* 2014 February; 66:110-6. doi: 10.1016/j.addr.2013.12.008. Epub 2013 Dec. 30, which describes use of liposomes and nanoparticles for delivery means, the contents of each of which is incorporated herein by reference.

Labeling agents may be used in methods of the invention to determine the location of MCJ polypeptides in cells and tissues and also, may be used to assess the cell, tissue, or organelle location of treatment compounds that have been administered. Procedures for attaching and utilizing labeling agents such as enzymatic labels, dyes, radiolabels, etc. are well known in the art.

Effective Amounts for Treatment Methods

MCJ-modulating compounds of the invention, (e.g., that comprise an anti-MCJ antibody or functional fragment thereof, a variant MCJ polypeptide-encoding polynucleotide, a variant MCJ polypeptide, a small molecule MCJ inhibitor molecule, etc.) are administered to a subject in an effective amount for treating the drug-induced disease or condition. An "effective amount for treating a drug-induced disease or condition" is an amount necessary or sufficient to realize a desired biologic effect. For example, an effective amount of a compound of the invention could be that amount necessary to (i) slow or halt progression of the disease or condition; or (ii) reverse, reduce, or eliminate one or more symptoms of the drug-induced disease or condition. In some aspects of the invention, an effective amount is that amount of an MCJ-inhibiting compound that when administered to a subject in need of a treatment of a drug-induced disease or condition, results in a therapeutic response that prevents and/or treats the drug-induced disease or condition. According to some aspects of the invention, an effective amount is that amount of an MCJ-inhibiting compound that when combined or co-administered with another therapeutic treatment for a drug-induced disease or condition, results in a therapeutic response that prevents and/or treats the drug-induced disease or condition. In some embodiments of the invention, a biologic effect of treating a subject with an MCJ-inhibiting compound may be the amelioration and or absolute elimination of symptoms resulting from the drug-induced disease or condition. In some embodiments of the invention, a biologic effect is the complete abrogation of the drug-induced disease or condition, as evidenced for example, by a diagnostic test that indicates the subject is free of the drug-induced disease or condition.

Typically an effective amount of an MCJ-inhibitor compound to decrease MCJ polypeptide activity will be determined in clinical trials, establishing an effective dose for a test population versus a control population in a blind study. In some embodiments, an effective amount will be that results in a desired response, e.g., an amount that diminishes a drug-induced disease or condition in cells, tissues, and/or subjects with the drug-induced disease or condition. Thus, an effective amount to treat a drug-induced disease or condition that can be treated by reducing MCJ polypeptide activity, may be the amount that when administered decreases the amount of MCJ polypeptide activity in the subject to an amount that that is less than the amount that would be present in the cell, tissue, and/or subject without the administration of the MCJ-inhibiting molecule. In certain aspects of the invention the level of MCJ activity present in a cell, tissue, and/or subject that has not been contacted with or administered a MCJ-inhibiting compound is referred to as a "control" amount. In the case of treating a drug-induced disease or condition the desired response may be reducing or eliminating one or more symptoms of the drug-induced disease or condition in the cell, tissue, and/or subject. The reduction or elimination may be temporary or may be permanent. It will be understood that the status of a drug-induced disease or condition can be monitored using methods of determining MCJ polypeptide activity, symptom evaluation, clinical testing, etc. In some aspects of the invention, a desired response to treatment of the drug-induced disease or condition also can be delaying the onset or even preventing the onset of the drug-induced disease or condition.

An effective amount of a compound that decreases MCJ polypeptide activity may also be determined by assessing physiological effects of administration of the compound on a cell or subject, such as a decrease of a drug-induced disease or condition following administration. Assays and/or symptomatic monitoring of a subject can be used to determine efficacy of a pharmaceutical compound of the invention and to determine the presence or absence of a response to a treatment. An example, though not intended to be limiting: is the use of an art-known test of liver function to determine the status of a drug-induced disease or condition in a subject before and after treatment of the subject with an MCJ-inhibiting compound. It will be understood that the amount of an MCJ-inhibiting compound that is administered to a subject can be modified based, at least in part, on such determinations of disease and/or condition status. The amount of a treatment may be varied for example by increasing or decreasing the amount of an MCJ-inhibiting compound, by changing the composition of the MCJ-inhibiting compound administered, by changing the route of administration, by changing the dosage timing and so on. The effective amount of an MCJ-inhibiting compound will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner. For example, an effective amount may depend upon the desired level of MCJ polypeptide activity that is effective to treat the drug-induced disease or condition. A skilled artisan can empirically determine an effective amount of a particular MCJ-inhibiting compound of the invention without necessitating undue experimentation. Combined with the teachings provided herein, by selecting from among various MCJ-inhibiting compounds and weighing factors such as potency, relative bioavailability, patient body weight, severity of adverse side-effects and preferred mode of administration, an effective prophylactic or therapeutic treatment regimen can be planned that is effective to treat the particular subject.

An MCJ-inhibiting compound that is administered using methods of the invention is also referred to herein as a "pharmaceutical compound". A pharmaceutical compound dosage may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Methods of the invention may in some embodiments include administering 1, 2, 3, 4, 5, 6, 7, 8, 9, 10, or more doses of an MCJ-inhibitor compound. In some instances, a pharmaceutical compound of the invention, (e.g., an anti-MCJ antibody or functional fragment thereof, a variant MCJ polypeptide-encoding polynucleotide, a variant MCJ polypeptide, a small molecule MCJ inhibitor, such as an RNA interference molecule, etc.) can be administered to a subject at least daily, every other day, weekly, every other week, monthly, etc. Doses may be administered once per day or more than once per day, for example, 2, 3, 4, 5, or more times in one 24 hour period. As described elsewhere herein, an MCJ-inhibitor compound may be administered to a subject in advance of administration to the subject of an agent known to induce a drug-induced disease or condition, in conjunction with an administration to the subject of an agent known to induce a drug-induced disease or condition, after administration to the subject of an agent known to induce a drug-induced disease or condition, or any combination of these times.

Methods of the invention, in some aspects, include administration of a pharmaceutical compound alone, in combination with one or more other MCJ-inhibiting compounds, and/or in combination with other drug therapies or treatment regimens that are administered to subjects with a drug-induced disease or condition. Pharmaceutical compounds may be administered in pharmaceutical compositions. Pharmaceutical compositions used in methods of the invention may be sterile and contain an amount of an MCJ-inhibiting compound that will reduce an MCJ polypeptide activity to a level sufficient to produce the desired response in a unit of weight or volume suitable for administration to a subject. A dose administered to a subject of a pharmaceutical composition that includes an MCJ-inhibiting compound to reduce MCJ polypeptide activity can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for a MCJ-inhibiting compound are available for use in methods of the invention. The particular delivery mode selected will depend at least in part, upon the particular condition being treated and the dosage required for therapeutic efficacy. Methods of this invention, generally speaking, may be practiced using any mode of administration that is medically acceptable, meaning any mode that produces effective levels of treatment of a drug-induced disease or condition without causing clinically unacceptable adverse effects. In some embodiments of the invention, an MCJ-inhibiting compound may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, a compound of the invention may be placed within a slow release matrix and administered by placement of the matrix in the subject. In some aspects of the invention, an MCJ-inhibiting compound (such as an anti-MCJ antibody or functional fragment thereof, a variant MCJ polypeptide-encoding polynucleotide, a variant MCJ polypeptide, or a small molecule MCJ inhibitor, etc.) may be delivered to a subject cell using nanoparticles coated with an delivery agent that targets a specific cell or organelle, a non-limiting example of which is a mitochondrion. Various delivery means, methods, agents are known in the art. Non-limiting examples of delivery methods and delivery agents are additionally provided elsewhere herein.

In some methods of the invention one or more MCJ-inhibiting compounds may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments of the invention an MCJ-inhibiting compound may be formulated with a pharmaceutical agent for simultaneous administration. Non-limiting examples are formulations that include an MCJ-inhibiting compound and an acetaminophen compound, and formulations that include an MCJ-inhibiting compound and a contrast dye. According to methods of the invention, an MCJ-inhibiting compound may be administered in a pharmaceutical composition. In general, a pharmaceutical composition comprises an MCJ-inhibiting compound and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the compound such as an anti-MCJ antibody or functional fragment thereof, variant MCJ polypeptide-encoding polynucleotide, variant MCJ polypeptide, or a small molecule MCJ inhibitor molecule, etc. to treat the drug-induced disease or condition. Numerous methods useful to administer and deliver antibodies, polypeptides, polynucleotides, small molecules, RNAi molecules, etc. for therapeutic use are known in the art.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Some embodiments of methods of the invention include administering one or more MCJ-inhibiting compounds directly to a tissue. In some embodiments, the tissue to which the compound is administered is a tissue in which the drug-induced disease or condition is likely to arise, non-limiting examples of which are the liver, kidney, cardiac tissue. Direct tissue administration may be achieved by direct injection or other means. Many orally delivered compounds naturally travel to and through the liver and kidneys some embodiments of treatment methods of the invention include oral administration of one or more MCJ-inhibiting compounds to a subject. MCJ-inhibiting compounds, either alone or in conjunction with other agents, may be administered once, or alternatively they may be administered in a plurality of administrations. If administered multiple times, the compounds may be administered via different routes. For example, though not intended to be limiting, a first (or first several) administrations may be made via oral administration and one or more additional administrations may be oral and/or systemic administrations.

For embodiments of the invention in which it is desirable to administer an MCJ-inhibiting compound systemically, the MCJ-inhibiting compound may be formulated for parenteral administration by injection, e.g., by bolus injection or continuous infusion. Formulations for injection may be presented in unit dosage form, e.g., in ampoules or in multi-dose containers, with or without an added preservative. The MCJ-inhibiting compound formulations (also referred to as pharmaceutical compositions) may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more MCJ-inhibiting compounds.

In yet other embodiments, methods of the invention include use of a delivery vehicle such as biocompatible microparticle, nanoparticle, or implant suitable for implantation into the recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of an MCJ-inhibiting molecule in a subject, and may be selected not to degrade, but rather, to release by diffusion over an extended period of time.

Both non-biodegradable and biodegradable polymeric matrices can be used in methods of the invention to deliver one or more MCJ-inhibiting compounds to the subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, MCJ-inhibiting compounds may be delivered in some embodiments of the invention using the bioerodible implant by way of diffusion, or by degradation of the polymeric matrix. Exemplary synthetic polymers for such use are well known in the art. Biodegradable polymers and non-biodegradable polymers can be used for delivery of MCJ-inhibiting compounds using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver MCJ-inhibiting compounds for treatment of a drug-induced disease or condition. Additional suitable delivery systems can include time-release, delayed release or sustained release delivery systems. Such systems can avoid repeated administrations of an MCJ-inhibiting compound, increasing convenience to the subject and the medical care professional. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be suitable for prophylactic treatment of subjects and for subjects at risk of developing a recurrent drug-induced disease or condition, for example subjects receiving an ongoing treatment with a pharmaceutical agent that has a known side-effect of inducing a drug-induced disease or condition. Long-term release, as used herein, means that the implant is constructed and arranged to deliver a therapeutic level of an MCJ-inhibiting compound for at least 30 days, 60 days, 90 days or longer. Long-term sustained release implants are well-known to those of ordinary skill in the art and include some of the release systems described above.

Therapeutic formulations of MCJ-inhibiting compounds may be prepared for storage by mixing the molecule or compound having the desired degree of purity with optional pharmaceutically acceptable carriers, excipients or stabilizers [Remington's Pharmaceutical Sciences $21^{st}$ edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Assessing Treatments

Assessment of efficacy of candidate MCJ-inhibiting molecules and compounds to decrease activity of an MCJ polypeptide in a cell or tissue may also be done using assays of the invention in cells from culture—e.g., as screening assays to assess candidate MCJ-inhibiting compounds for their ability to reduce MCJ polypeptide activity. MCJ-inhibiting compounds that reduce MCJ polypeptide activity in a cell, tissue, or subject may be used in the treatment of a drug-induced disease or condition or as a pretreatment for a drug-induced disease or condition (e.g., to prepare a cell or subject for subsequent treatment with an agent known to induce a drug-induced disease or condition).

Suitable assays may include means to determine MCJ polypeptide activity, including but not limited to determining levels of polynucleotides that encode MCJ polypeptides and/or determining levels of MCJ polypeptides and/or MCJ polypeptide activity in cells, tissues, and subjects. Levels of MCJ polypeptide-encoding polynucleotides and polypeptides and their activity can be determined in a number of ways when carrying out the various methods of the invention. In some embodiments of the invention, a level of MCJ polypeptide-encoding polynucleotide or polypeptide or their activity is measured in relation to a control level of MCJ-polypeptide-encoding polynucleotide or polypeptide or their activity, respectively, in a cell, tissue, or subject. One possible measurement of a level of MCJ polypeptide-encoding polynucleotide or polypeptide is a measurement of an absolute level of the MCJ-polypeptide-encoding polynucleotide or polypeptide. This could be expressed, for example, in MCJ-polypeptide-encoding polynucleotide or polypeptide per unit of cells or tissue. Another measurement of a level of MCJ polypeptide-encoding polynucleotide or polypeptide is a measurement of the change in the level and/or activity of MCJ-polypeptide-encoding polynucleotide or polypeptide over time. This may be expressed in an absolute amount or may be expressed in terms of a percentage increase or decrease over time. Activity assays for MCJ polypeptides may also be used to assess efficacy of an MCJ-inhibitor molecule or compound. In addition, in certain embodiments of the invention, an antibody or antigen-binding fragment thereof, or other compound that specifically binds MCJ polypeptides may be used to assess a level of MCJ polypeptides present after treatment with an MCJ inhibitor compound.

In some embodiments of the invention, a decrease in an MCJ polypeptide activity level in a cell or tissue, may be a decrease of more than 0.2%, more than 0.5%, more than 1.0%, 2.0%, 3.0%, 4.0%, 5.0%, 7.0%, 10%, 15%, 20%, 25%, 30%, 40%, 50%, 60%, 70%, 80%, 90%, or 100% including all values in this range. A decrease in MCJ polypeptide activity after contact with an MCJ-inhibiting compound may indicate efficacy of the MCJ-inhibiting compound to treat a drug-induced disease or condition in a subject.

As will be appreciated by those of ordinary skill in the art, the evaluation of a treatment of the invention also may be based upon an evaluation of the symptoms or clinical end-points of a drug-induced disease or condition and such evaluations can be used in conjunction with methods of the invention to assess the status of a drug-induced disease or condition and/or the efficacy of a treatment of a drug-induced disease or condition. Antibodies or antigen-binding fragments or other compounds that specifically bind MCJ polypeptides may be used to assess a level of MCJ polypeptides after treatment with an MCJ inhibitor compound. Antibodies or antigen-binding fragments or other compounds that specifically bind MCJ polypeptides may be used to assess a level of MCJ polypeptides after administration of an MCJ inhibitor compound in a treatment method of the invention.

Kits

Also within the scope of the invention are kits that comprise MCJ-inhibiting compounds and instructions for their use in methods of the invention. Kits of the invention may include one or more of an MCJ-inhibiting compound such as an anti-MCJ antibody or functional fragment thereof, a variant MCJ polypeptide-encoding polynucleotide, a variant MCJ polypeptide, or a small molecule MCJ inhibitor, etc., which may be used to treat a drug-induced disease or condition. Kits containing MCJ-inhibiting compounds can be prepared for use in treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more compounds such as an anti-MCJ antibody or functional fragment thereof, a variant MCJ polypeptide-encoding polynucleotide, a variant MCJ polypeptide, or a small molecule MCJ inhibitor, etc. A second container means or series of container means may contain a targeting agent, a labelling agent, a delivery agent, etc. that may be included as a portion of an MCJ-inhibiting compound administered in an embodiment of a treatment method of the invention.

A kit of the invention may also include instructions. Instructions typically will be in written form and will provide guidance for carrying-out a treatment embodied by the kit and for making a determination based upon that treatment.

Methods to Identify Candidate Compounds

Certain aspects of the invention include methods of identifying and/or screening candidate compounds that reduce MCJ polypeptide activity in cells, tissues, and/or subjects. Methods can include contacting a candidate compound with cells or tissues and/or administering the candidate compound to a subject and determining an amount of MCJ polypeptide activity before and after contact of the cells, tissues, and/or subject with the candidate compound. A decrease in the amount of MCJ polypeptide activity in comparison to a suitable control is indicative of a compound capable of decreasing the level of MCJ.

An assay mixture useful to assess a treatment candidate for a drug-induced disease or disorder comprises a candidate compound. The candidate compound may be an antibody, a small organic compound, small molecule, polypeptide, DNA molecule, RNA molecule, etc., and accordingly can be selected from combinatorial antibody libraries, combinatorial protein libraries, small organic molecule libraries, or any other suitable source. A candidate DNA or RNA molecule may be designed based on art-recognized parameters for molecules useful to reduce gene expression. Typically, to test candidate compounds, a plurality of reaction mixtures is run in parallel with different compound concentrations to obtain a different response to the various concentrations. Typically, one of these concentrations serves as a negative control, i.e., at zero concentration of compound or at a concentration of compound below the limits of assay detection.

A variety of other reagents also can be included in an assay mixture to test a candidate compound. These may include reagents such as salts, buffers, neutral proteins (e.g., albumin), detergents, etc., which may be used to facilitate optimal protein-protein and/or protein-compound binding. Such a reagent may also reduce non-specific or background interactions of the reaction components. Other reagents that improve the efficiency of the assay such as protease inhibitors, nuclease inhibitors, antimicrobial agents, and the like may also be used. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times may be minimized to facilitate rapid, high throughput screening, and typically are between 0.1 and 10 hours. After incubation, variables such as the presence, amount of an MCJ polypeptide, and/or the activity of an MCJ polypeptide can be detected by any convenient method available to the user. For example, the amount and/or activity of a MCJ polypeptide after contact with a candidate compound can be determined using standard methods and as described herein.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Experiments and studies were performed to assess the effects of reducing activity of MCJ (DnaJC15) on drug-induced damage and injury in cells, organs, and organ systems. The results indicated that in the absence of MCJ there is increased mitochondrial function in the liver. Studies were performed in a mouse model of liver cirrhosis (Bile Duct Ligation, BDL) in MCJ knockout mice and the results demonstrated that MCJ deficiency protected the mice from the development of fibrosis. Experiments that included a mouse model for drug-induced liver injury (DILI) with administration of high doses of acetaminophen, demonstrated that MCJ knockout mice were more resistant to DILI than mice that had normal MCJ polypeptide expression/activity. In addition, experiments were performed that demonstrated that treatment with siRNA for MCJ protected wild-type cells from drug-induced (toxic) injury. Results showed that siRNA for MCJ protected wild-type hepatocytes from the development of toxic injury caused by administration of acetaminophen.

Material and Methods

Human Samples

Forty-seven patients with liver cirrhosis and hepatocellular carcinoma (HCC) with preserved liver function and corresponded to either Barcelona Clinic Liver Center (BCLC) stage A (n=34) and B (n=13) were provided by Dra. Erica Villa (University of Modena and Reggio Emilia, Modena, Italy). Healthy human liver samples were used as controls (n=13). Further information is provided in the original study (Villa, E. et al., 2015, Neoangiogenesis-related genes are hallmarks of fast-growing hepatocellular carcinomas and worst survival. Results from a prospective study. Gut. 2015 Feb. 9. doi: 10.1136/gutjnl-2014-308483—Epub). Informed consent was obtained from all the patients included in the study, accordingly with the ethical principles embodied in the Declaration of Helsinki.

Animals.

Three-month-old male (C57BL6), MCJ wild type (WT) and MCJ-knockout (KO) mice were used in the study. Animal procedures were approved following the CIC bioGUNE Animal Facility's guidelines with AAALAC certificate.

Immunohistochemistry

Paraffin embedded liver samples were sectioned, dewaxed and hydrated. All procedures were done according to standard protocols with EnVision+System HRP (Dako, Denmark). Finally, samples were incubated with Vector Vip substrate (Vector, USA) for color development. Images were taken with a 10× or 20× objective from a microscope AXIO Imager A1 (Carl Zeiss AG, Germany). Quantification of staining intensity, average sum of intensities and stained area percentage of each sample were calculated using FRIDA software (FRamework for Image Dataset Analysis) http://bui3.win.ad.jhu.edu/frida/.

RNA Isolation and Real-Time Polymerase Chain Reaction (RT-PCR).

Total RNA was isolated using Trizol (Invitrogen, USA). One to two μg of total RNA was treated with DNAse (Invitrogen) and reverse transcribed into cDNA using M-MLV Reverse Transcriptase (Invitrogen). Then, qPCR was performed using iQ™ SYBR® Green Supermix (Bio-Rad, USA) using the CFX Connect™ RT-PCR Detection System (BioRad). Expression levels were normalized to the average level of GAPDH mRNA in each sample.

Animal Cirrhosis Experimental Models and In Vivo Drug Treatment

MCJ wild type (WT) and MCJ-knockout (KO) mice bred in the animal facility at the CIC bioGUNE were used. Animal procedures were approved by the CIC bioGUNE Animal Care and Use Committee. Bile duct ligation was performed as previously described (Fernández-Álvarez S, et al., (2015) Lab Invest. 95, 223-36.). At least 5 animals per group were used.

Characterization of Liver Damage

Alanine aminotransferase (ALT) aspartate aminotransferase (AST) and bilirubin were determined in serum samples using the Selectra Junior SpinLab 100 analyzer (Vital Scientific) and the SpinReact reagents according to manufacturer's protocols.

Isolation and Culture of Primary Hepatocytes.

Primary hepatocytes were isolated from male WT MCJ-KO mice via collagenase perfusion as described (see: Barbier-Torres L, et al., (2015) Oncotarget. 6, 2509-23). Adhered cells were maintained in MEM with 10% fetal bovine serum (FBS).

Measurements of Oxygen Consumption Rate and Extracellular Acidification Rate

Primary MCJ-WT mouse hepatocytes were seeded respectively in a collagen I coated XF24 cell culture microplate (Seahorse Bioscience), at $2.0 \times 10^4$ cells per well. Measurements of oxygen consumption rate (OCR) and extracellular acidification rate (ECAR) were performed after equilibration in assay medium for 1 h. After an OCR and ECAR baseline measurement, oligomycin (1 μM), carbonyl cyanide 4-(trifluoromethoxy) phenylhydrazone (FCCP) (3 μM) and rotenone (RO) (1 μM) solutions were sequentially added to each well to reach working concentrations, and changes in the OCR and ECAR were analyzed. The normalize data were expressed as pmol of $O_2$ per minute or milli-pH units (mpH) per minute, perm protein for primary hepatocytes.

In Vitro Silencing

Primary MCJ-WT mouse hepatocytes were transfected with 2 mg of shMCJ or unrelated ShControl using Jetprime reagent (Polyplus) for 24 hours. Certain of the experiments included use of an shMCJ that included an siRNA having SEQ ID NO: 22 that was included in and delivered as part of a plasmid per standard shRNA procedures. Primary hepatocytes were treated with Deoxycholic acid (DCA) 100 mM for two hours. Triplicates were used in each experiment.

Apoptosis Measurement

Caspase 3 activity assay was performed as previously described [Barbier-Torres L, et al., (2015) Oncotarget. 6, 2509-23].

Statistical Analysis

All experiments were performed in triplicate. Data are expressed as mean±SEM. Statistical significance was estimated with Student's t test. A p value <0.05 was considered significant.

Results

Figure 1B:
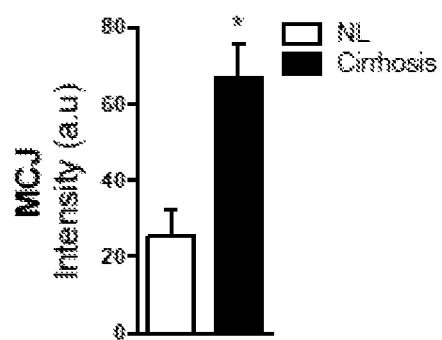

Results indicated that there was an increase in MCJ levels in liver in subjects with cirrhosis. FIG. 1A-B shows photomicrographic images and a graph demonstrating that livers of cirrhosis patients had increased MCJ levels. Immunohistochemistry results in FIG. 1A, left panel show MCJ expression in liver from healthy control subjects (NL) (n=5) and in FIG. 1A, MCJ expression in liver from patients (n=16) with cirrhosis (hepatitis C). FIG. 1B is a graph showing levels of MCJ expression determined for the healthy and the cirrhosis patients. The results show a statistically significant increase in the levels of MCJ in cirrhotic livers.

Results of experiments performed to assess effect of the presence of MCJ on severity of liver injury in a mouse model of drug-induced liver injury (DILI) demonstrated that a decreased level of MCJ resulted in a reduced amount of drug-induced liver injury versus the amount of drug-induced liver injury in a wild-type mouse with a normal MCJ level. FIG. 2A-B provides photomicrographic images and graphs showing use of acetaminophen administration as a mouse model for drug-induced liver injury (DILI). Results are shown for wild-type (WT) and MCJ knock-out (KO) mice that were administered acetaminophen i.p. FIG. 2A shows results after 48 hours and shows the presence of macrophages in liver sections that were examined by immunohistochemistry for F4/80 macrophage marker. FIG. 2A (left panel) is representative of WT, FIG. 2A (right panel) is representative for MCJ KO. FIG. 2B, right graph shows the levels of ALT and AST transaminase in serum. FIG. 2B (left panel) is representative of one mouse for each genotype. FIG. 2B (right panel) shows the value for n=4 mice for each genotype. Results indicated that the KO mice were more resistant to the damage induced by acetaminophen in the liver. FIG. 2B left panel shows lower F4/80 macrophage marker in the KO mice. The MCJ KO mice developed less inflammation and had lower levels of transaminases than the WT mice.

Figure 3A:
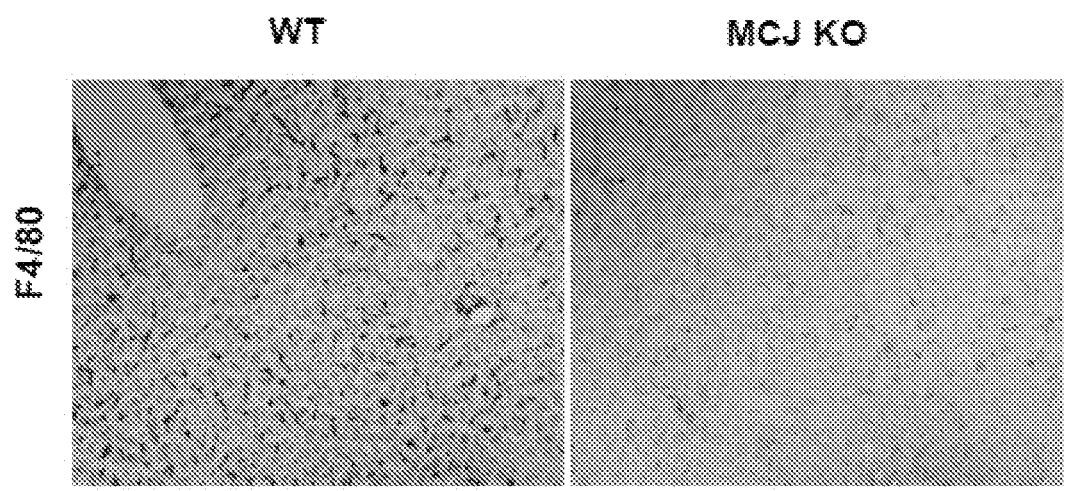
FIG. 3A-C shows results from WT and MCJ KO mice that underwent bile duct ligation surgery, utilizing duct ligation (BDL) mouse model for cirrhosis.
Figure 3B:
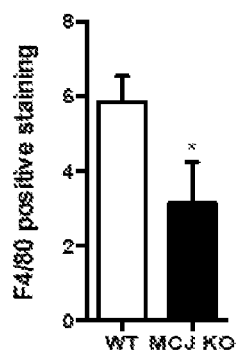
Figure 3C:
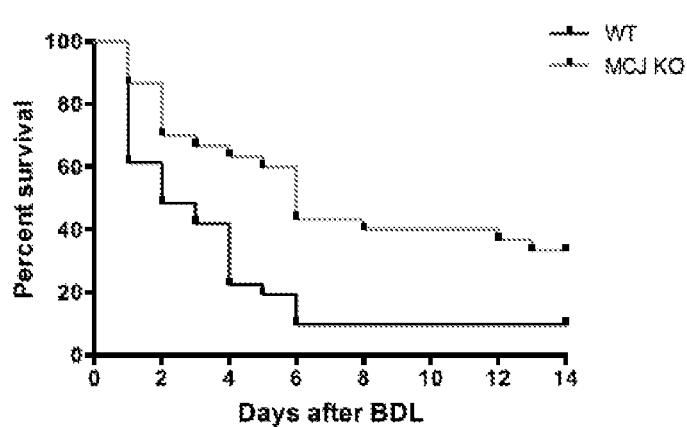
Figure 4A:
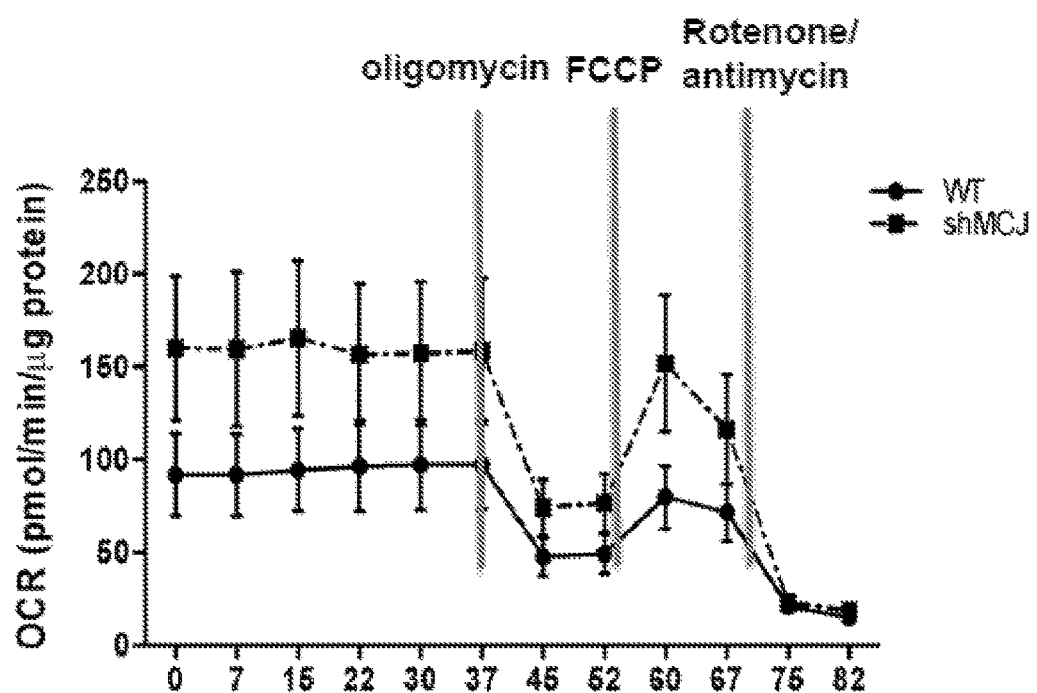
FIG. 4A shows oxygen consumption rate (OCR) values in primary hepatocytes from WT mice transfected with control (WT) or shMCJ (shMCJ) expressing plasmids. The results showed that shMCJ treatment reduced the OCR compared to WT.
Figure 4B:
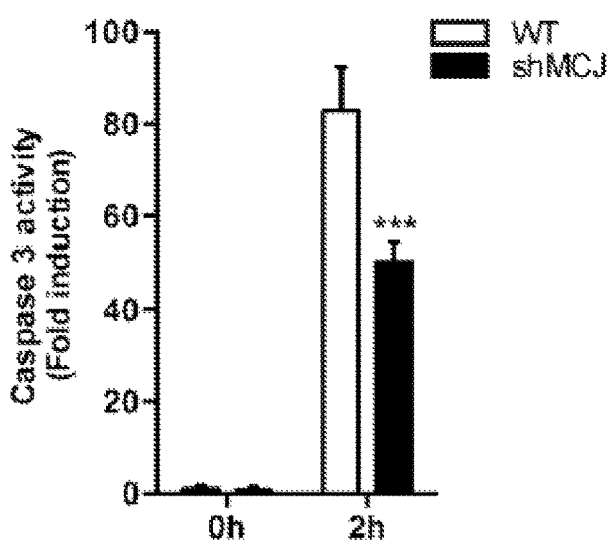
FIG. 4B shows Caspase-3 activity (marker for cell death) after DCA 100 µM treatment in primary hepatocytes from WT mice transfected with control (WT) or shMCJ (shMCJ) expressing plasmids. The results indicated that treatment with shMCJ reduced Caspase-3 activity compared to WT.

Results of experiments performed to assess effect of the presence of MCJ on severity of cirrhosis-type liver damage in a mouse model of cirrhosis-type liver damage demonstrated that a decreased level of MCJ resulted in a reduced amount of cirrhosis-type liver damage versus the amount of cirrhosis-type liver damage in a wild-type mouse with a normal MCJ level. FIG. 3A-C shows results from WT and MCJ KO mice that underwent bile duct ligation surgery, utilizing duct ligation (BDL) mouse model for cirrhosis. FIG. 3A shows photomicrographic images of the liver after 14 days. Tissue damage was indicated by the presence of macrophages (F4/80) by IHC as a marker of the inflammation. FIG. 3A, left panel is image from one WT one mouse and FIG. 3A, right panel is image from one MCJ KO mouse. FIG. 3B is a graph showing the F4/80 positive staining value for n=4 mice for each genotype. FIG. 3C provides a survival curve for WT and MCJ KO mice upon bile duct ligation surgery. MCJ KO mice are more resistant to develop cirrhosis-type of liver damage Results of experiments performed to measure oxygen consumption rate (OCR) values in liver cells to assess whether administration of MCJ shRNA would protect liver cells from cirrhosis-type damage. The administration of MCJ shRNA reduced the amount of cirrhosis-type damage compared to the level of cirrhosis-type damage in wild-type mice not administered MCJ shRNA. FIG. 4A-B provides graphs showing that MCJ shRNA (shMCJ) protected primary hepatocytes from DCA-induced death. FIG. 4A shows oxygen consumption rate (OCR) values in primary hepatocytes from WT mice transfected with control (WT) or shMCJ (shMCJ) expressing plasmids. The results showed that shMCJ treatment reduced the OCR compared to WT. FIG. 4B shows Caspase-3 activity (marker for cell death) after DCA 100 μM treatment in primary hepatocytes from WT mice transfected with control (WT) or shMCJ (shMCJ) expressing plasmids. The results indicated that treatment with shMCJ reduced Caspase-3 activity compared to WT.

Example 2

Mitochondria are the main energy source in hepatocytes and play a major role in extensive oxidative metabolism and normal function of the liver. They control signaling pathways that mediate hepatocyte injury, since impaired mitochondrial functions affect cell survival and contribute to liver disease. Notably, altered mitochondrial functions have been documented in a variety of chronic liver diseases including drug-induced liver injury (DILI). The goal of the studies was to determine whether MCJ, a endogenous negative regulator of mitochondrial respiration, has an effect on DILI and the development of drugs that can inhibit MCJ function to protect or cure liver injury.

Materials and Methods

See Materials and Methods in Example 1 for additional methods and details.

Liver Histology and Immunohistochemistry for MCJ

Paraffin-embedded liver samples were sectioned, dewaxed, and hydrated. Immunohistochemistry (IHC) was performed using an anti-MCJ antibody and nuclei were counter-stained with hematoxylin. Quantification of staining area of each sample was analyzed using the Frida software and represented as the % of the stained area relative to the total area (power field). Ten fields per sample were pictured and analyzed. For liver histology, liver sections from paraffin-embedded tissue were stained with hematoxylin and eoxin (H&E staining). Frida software was used for quantification.

Analyses in Primary Mouse Hepatocytes.

Primary hepatocytes were isolated from WT and MCJ KO mice via collagenase perfusion. Cells were cultured in MEM media and treated with acetaminophen 10 mM for different time points. ATP levels were measured using the kit ATPLite (Perkin Elmer). Mitochondrial ROS was measured with MitoSOX reagent (Thermo Fisher Scientific) used for fluorescence microscopy analysis. Cell death was quantified with the TUNEL assay (Roche).

Western Blotting Analysis.

Analysis for MCJ expression in liver by Western blot analysis was performed as previously described (REF) using a specific anti-MCJ antibody. Expression of GAPDH was used as a control. Band intensities were quantified using the ImageJ software and normalized to the control (GAPDH).

Intravenous (i.v.) Administration of siRNA.

siMCJ oligos (double strand RNA oligos, see for example, SEQ ID NO: 22) containing the designed sequence were synthesized for in vivo studies (Ambion invivo siRNA). As a delivery system Invivofectamine 3.0 (Life Technology) was used because it is claimed to obtain high efficiency of in vivo delivery of siRNA into hepatocytes. Following the recommendation of the manufacturer, 1.7 mg/Kg was used in combination with invivofectamine 3.0. Preparation of siRNA with the Invivofectamine was performed as recommended by the manufacturer. Mice were administered with a single i.v. dose of siMCJ/invivofectamine in 150 µl.

Results

Increased MCJ Expression in Liver Caused by Drug-Induced Liver Injury (DILI) in Human and Mice.

Figure 5A:
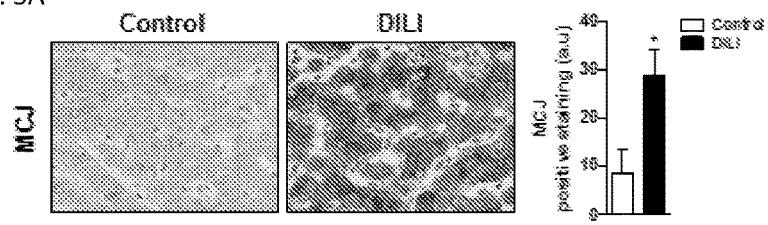
FIG. 5A-B provides micrographic images and graphs illustrating MCJ expression examined by immunohistochemistry followed by further quantification.

Because mitochondrial function is severely impaired in liver of patients with Drug-Induced Liver Injury (DILI), MCJ expression was examined in liver biopsy obtained from these patients as well as healthy control subjects. Expression was examined by immunohistochemistry followed by further quantification (see Methods). The results revealed that MO expression was statistically higher in liver from DILI patients (FIG. 5A).

Figure 5B:
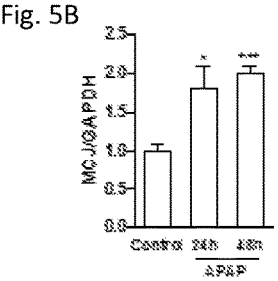

The expression of MCJ in the mouse liver was also examined using a mouse model of DILI where a single high dose of acetaminophen (APAP) is provided to the mice, leading to severe liver damage (high transaminases, tissue damage) within 36-48 h. Acetaminophen-induced liver injury is the second most common cause of acute liver failure, often requiring liver transplant as only treatment. Analysis of MCJ expression as determined by Western blot analysis showed significantly higher levels of MCJ in liver from APAP-treated mice compared with control mice (FIG. 5B).

Together these data showed that drug-induced liver damage causes an increase in MCJ levels in the liver both in human patients and in mice. These data also suggested that disrupting MCJ expression and/or function could be used as a therapeutic approach.

Lack of MCJ Protects Hepatocytes from Acetaminophen-Induced Mitochondria Dysfunction and Death.

Figure 6A:
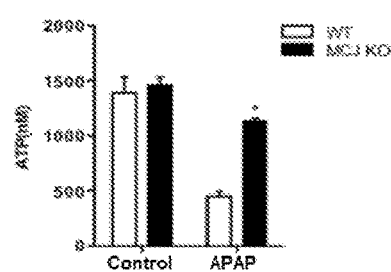
FIG. 6A-C provides graphs from studies demonstrating that MCJ protected hepatocytes from acetaminophen-induced mitochondria dysfunction and death.
Figure 6B:
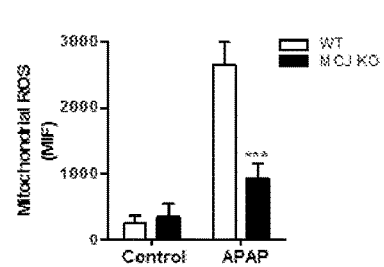
Figure 6C:
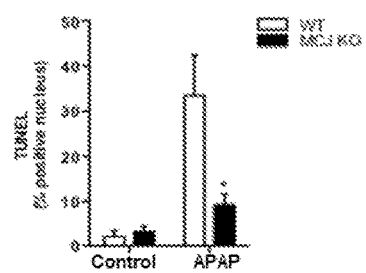

Considering the negative role of MCJ in mitochondria function and the elevated expression of MCJ in livers with DILI, studies were performed to investigate whether the lack of MCJ could protect mitochondria function in hepatocytes upon treatment with acetaminophen (APAP). Hepatocytes were isolated from livers of WT mice or MCJ KO mice and treated with APAP. As fast as 9 h after treatment the levels of ATP in WT hepatocytes were markedly low in WT hepatocytes, but remained higher in MCJ KO hepatocytes (FIG. 6A). It has been previously shown that APAP leads to generation of mitochondrial ROS and this is a cause that mediates hepatocyte cell death. Unexpectedly, lack of MO in MCJ KO hepatocytes prevented the generation of ROS (FIG. 6B). Thus, lack of MCJ is sufficient to maintain normal mitochondrial function in hepatocytes in response to APAP, and prevents the generation of ROS. Correlating with these effects, MCJ KO hepatocytes were found to be more resistant to cell death caused by APAP (FIG. 6C).

These data support a conclusion that disrupting MCJ expression and/or function can protect liver from drug-induced damage.

MCJ siRNA (siMCJ) Can be Used to Disrupt MCJ Expression in Liver In Vivo (Pharmacodynamics).

Figure 7:
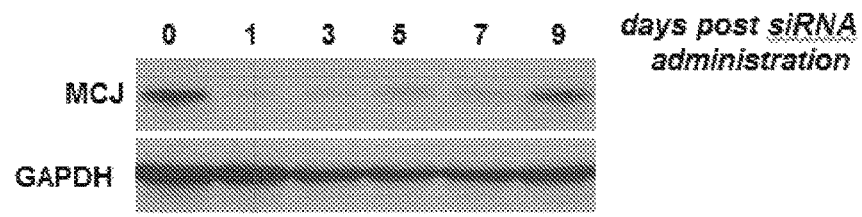
FIG. 7 provides a blot of results demonstrating that MCJ siRNA (siMCJ) could be used to disrupt MCJ expression in liver in vivo. Wild-type mice were administered siMCJ (1.7 mg/Kg) in combination with Invivofectamine through i.v. injection. Each mouse was harvested at the indicated time after the administration. Liver was harvested and MCJ expression was determined by Western blot analysis. GAPDH was used as loading control.

Based on positive results from recent trial using siRNA to target liver molecules (REF), siRNA for MCJ (siMCJ) was used in a strategy to reduce the levels of MCJ in the liver. To determine the efficacy and pharmacodynamics of siMCJ pilot studies were performed in which wild-type mice maintain in normal conditions were administered a single i.v. dose of siMCJ in combination with invivofectamine (as a delivery system), and mice were then harvested at different periods of time. The levels of MCJ in the livers of those mice were examined by Western blot analysis. As soon as 24 h after the administration of siMCJ, the levels of endogenous MCJ in the liver were almost undetectable (FIG. 7). The levels of MCJ remained very low for at least 7 days, and even after 9 days of administration there was not a full restoration of MCJ levels (FIG. 7). Thus, siMCJ was highly efficient in suppressing MCJ protein expression for an extended period of time.

Administration of siMCJ Prevents the Acetaminophen-Induced Liver Damage.

Studies were performed to investigate the effect of siMCJ in DILI treatment using the acetaminophen (APAP) mouse model. The results described above herein show that MCJ expression can be targeted by administration of siMCJ. Therefore additional studies were performed that tested whether one single siMCJ administration could protect livers from damaged caused by administration of acetaminophen. Wild-type mice received a dose of siMCJ together with invivofectamine. Control mice did not receive siMCJ. After 20 h, all mice were then administered with a i.p. dose of acetaminophen as described above. Mice were harvested 24 h after acetaminophen administration. Levels of MCJ in the liver were examined by Western blot analysis. The levels of MCJ in APAP-mice treated with siMCJ were markedly reduced relative to APAP-mice that did not get siMCJ (FIG. 8A). At the time of harvesting, it was already obvious based on the color of the liver (lighter color in livers after acetaminophen administration) that mice treated with siMCJ could be protected from acetaminophen-induced damage. These observations were confirmed by histological analysis of liver tissue sections, where livers from APAP-mice show areas of clear tissue damage, but these areas were almost not detected in livers from APAP-mice treated with siMCJ (FIG. 8B). Quantification of the damage area in the livers provided evidence of the protective effect of siMCJ from acetaminophen-induced liver injury (FIG. 8C). Thus, blocking MCJ expression with siMCJ in vivo protects from the damaging effects of acetaminophen in the liver.

Treatment with siMCJ After Acetaminophen Prevented the Acetaminophen-Induced Liver Damage.

Figure 9A:
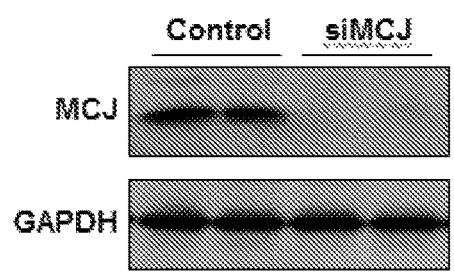
FIG. 9A-B shows a western blot and a graph illustrating that treatment with siMCJ after acetaminophen prevented the acetaminophen-induced liver damage. For the study, wild-type mice (n=3) were administered i.p. dose of acetaminophen (360 mg/Kg). 24 h later, mice received an i.v. injection of siMCJ (1.7 mg/Kg) in combination with invivofectamine 3.0. (siMCJ mice) or without siMCJ (Control mice). 24 h later (48 h total after the acetaminophen overdose) mice were harvested and liver and serum was collected.
Figure 9B:
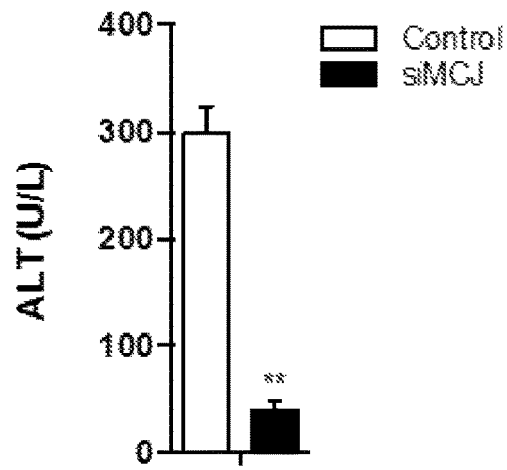

Currently, the only treatment for patients who are admitted into the intensive care unit with acute hepatic failure due to overdose of acetaminophen (the second leading cause of acute liver injury) is N-acetylcysteine (NAC). NAC has a hepatoprotective effect but only when administered within 8 h after the uptake of acetaminophen. After 8 h, the effect of NAC is minimal to known and the only option is liver transplant. To determine whether siMCJ could be used as a treatment in cases where patients after longer periods of time post-acetaminophen overdose, experiments were performed in which mice were first administered the high dose of acetaminophen. Then, 24 h later an i.v. injection with siMCJ and invivofectamine was given to a cohort of mice (siMCJ mice). 24 h later (48 h after administration of acetaminophen) mice were harvested and levels of MCJ in the livers were determined by Western blot analysis, and the levels of transaminases in blood was measured as a diagnosis for liver failure. The levels of MCJ in the liver in mice treated with siMCJ were almost undetectable (FIG. 9A), showing the efficacy to eliminate the presence of this protein the liver. More importantly, the levels of ALT (one of transaminases measured in patients) were drastically lower in mice that were treated with siMCJ (FIG. 9B).

Example 3

Figure 10:
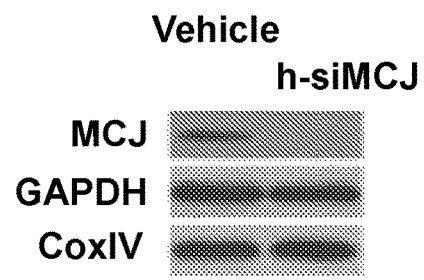
FIG. 10 shows a western blot illustrating reduction of MCJ in human MCF7 cells transfected with h-siMCJ. CoxIV (mitochondrial protein) and GAPDH levels were also examined as controls (Vehicle).

A human siMCJ has been tested in a human MCF7 cell line in vitro. Transfection of the human cell line cells with a small amount of h-siMCJ (SEQ ID NO: 21) was sufficient to knockdown MCJ protein expression (FIG. 10), while not affecting the levels of CoxIV, another mitochondrial protein. Transfection methods included transecting human MCF7 cells transfected with h-siMCJ (5 nM) and after 30 h cells were harvested and MCJ expression was examined by Western blot analysis using an anti-human MCJ antibody. CoxIV (mitochondrial protein) and GAPDH were also examined as controls. The results demonstrated the use of siRNA to reduce MCJ protein expression.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

What is claimed is:

1. A method for treating an acetaminophen-induced liver disease or condition in a subject, the method comprising administering to a subject in need of such treatment an MCJ-inhibiting compound in an amount effective to treat the acetaminophen-induced liver disease or condition in the subject, wherein the MCJ-inhibiting compound reduces MCJ polypeptide activity in the subject and decreasing the MCJ polypeptide activity comprises decreasing one or more of an MCJ polypeptide level or activity, and wherein the MCJ-inhibiting compound comprises am MCJ small interference RNA molecule (MCJ siRNA) or an MCJ small hairpin RNA molecule (MCJ shRNA).

2. The method of claim 1, wherein the disease or condition is an acute disease or condition.

3. The method of claim 1, wherein the MCJ-inhibiting compound further comprises a targeting agent, optionally a mitochondrial targeting agent.

4. The method of claim 1, wherein the MCJ siRNA molecule comprises a nucleic acid sequence set forth herein as SEQ ID NO: 21.

5. The method of claim 1, wherein the MCJ siRNA molecule comprises a nucleic acid sequence set forth herein as SEQ ID NO: 7.

6. The method of claim 1, wherein the MCJ-inhibiting compound is administered in a pharmaceutical composition, and wherein the pharmaceutical composition further comprises a pharmaceutically acceptable carrier and optionally comprises one or more of a carrier agent, a delivery agent, a labeling agent, and a targeting agent.

7. The method of claim 6, wherein the carrier agent comprises one or more of a nanocarrier, a cell-penetrating peptide, a polymer, a dendrimer, an siRNA bioconjugate, and a lipid-based siRNA carrier.

8. The method of claim 6, wherein the pharmaceutical composition additionally comprises acetaminophen.

9. The method of claim 1, wherein the MCJ-inhibiting compound is administered to the subject at one or more of before, concurrently with, and after ingestion by the subject of acetaminophen.

10. A method of reducing an acetaminophen-induced disease or condition in a liver cell, the method comprising contacting the liver cell with an MCJ-inhibiting compound in an amount effective to decrease an MCJ polypeptide activity in the liver cell, wherein decreasing the MCJ polypeptide activity comprises decreasing one or more of a level or function of an MCJ polypeptide in the liver cell, and wherein the MCJ-inhibiting compound comprises an MCJ small interference RNA molecule (MCJ siRNA) or an MCJ small hairpin RNA molecule (MCJ shRNA).

11. The method of claim 10, wherein the MCJ siRNA molecule comprises a nucleic acid sequence set forth herein as SEQ ID NO: 21.

12. The method of claim 10, wherein the MCJ siRNA molecule comprises a nucleic acid sequence set forth herein as SEQ ID NO:7.

13. The method of claim 10, wherein the cell is contacted with the MCJ-inhibiting compound in a pharmaceutical composition, and wherein the pharmaceutical composition further comprises a pharmaceutically acceptable carrier and optionally comprises one or more of a carrier agent, a delivery agent, a labeling agent, a targeting agent, and acetaminophen.

14. The method of claim 10, wherein the MCJ-inhibiting compound further comprises a targeting agent, optionally a mitochondrial targeting agent.

* * * * *

SEQUENCE LISTING

```
<160> NUMBER OF SEQ ID NOS: 23

<210> SEQ ID NO 1
<211> LENGTH: 150
<212> TYPE: PRT
<213> ORGANISM: Homo sapiens

<400> SEQUENCE: 1

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125
```

```
Gly Ser Pro Tyr Val Ala Ala Lys Ile Asn Glu Ala Lys Asp Leu Leu
            130                 135                 140

Glu Thr Thr Thr Lys His
145                 150

<210> SEQ ID NO 2
<211> LENGTH: 1074
<212> TYPE: DNA
<213> ORGANISM: Homo sapiens
<220> FEATURE:
<221> NAME/KEY: misc_feature
<222> LOCATION: (1)..(1074)
<223> OTHER INFORMATION: mRNA sequence (complete CDS) of human DNAJ
      domain-containing protein MCJ set forth as GENBANK Accession No.
      AF126743.1:

<400> SEQUENCE: 2
ggtcaggaaa gctcaggcaa gcccaccctc aggcattaca gctagactcc gagcttactg    60
ggcagtcatc tgattcgacc aacatcagtt cgcagggctt aagcccagtc ccttacggcg   120
gctggggagg gaccaggccc aagtatataa agctccctga gggtccgcgt tggctttgcg   180
cctgtgagtg tgattcaaga acgtcccagt gcccttggct cctttcggag tgtgaccccg   240
tgcttgcacg ggacacgtta cccagctcgg gtgagaaggg tatcttccgg gaacctcgcc   300
tttaatagca caacgagcgc agagtccact ggatctgcga gaagaaaccg cgctaactag   360
tttgtcccta cggccgcctc gtagtcactg ccgcggcgcc ttgagtctcc gggccgcctt   420
gccatggctg cccgtggtgt catcgctcca gttggcgaga gtttgcgcta cgctgagtac   480
ttgcagccct cggccaaacg gccagacgcc gacgtcgacc agcagggact ggtaagaagt   540
ttgatagctg taggactggg tgttgcagct cttgcatttg caggtcgcta cgcatttcgg   600
atctggaaac tctagaaca agttatcaca gaaactgcaa gaagatttc aactcctagc    660 ttttcatcct actataaagg aggatttgaa cagaaaatga gtaggcgaga agctggtctt   720
attttaggtg taagcccatc tgctggcaag gctaagatta gaacagctca taggagagtc   780
atgattttga atcacccaga taaggtggac tctccttacg tagcagccaa aataaatgaa   840
gcaaaagact tgctagaaac aaccaccaaa cattgatgct taaggaccac actgaaggaa   900 aaaaaagag gggacttcga aaaaaaaaaa agccctgcaa aatattctaa aacatggtct   960
tcttaatttt ctatatggat tgaccacagt cttatcttcc accattaagc tgtataacaa  1020
taaaatgtta atagtcttgc tttttattat ctttttaaaga tctccttaaa ttct        1074

<210> SEQ ID NO 3
<211> LENGTH: 149
<212> TYPE: PRT
<213> ORGANISM: Mus musculus

<400> SEQUENCE: 3

Met Ala Thr Gly Gly Val Thr Ser Arg Glu Ser Leu Arg Tyr Ala
1               5                   10                  15

Glu Tyr Leu Pro Pro Ser Ala Gln Arg Ser Asp Ala Asp Ile Asp His
                20                  25                  30

Thr Ala Gly Arg Arg Leu Ile Ala Val Gly Leu Gly Val Ala Ala Val
            35                  40                  45

Ala Phe Ala Gly Arg Tyr Ala Phe Gln Ile Trp Lys Pro Leu Glu Gln
        50                  55                  60

Val Ile Thr Ala Thr Ala Arg Lys Ile Ser Ser Pro Ser Phe Ser Ser
65                  70                  75                  80
```

```
Tyr Tyr Lys Gly Gly Phe Glu Gln Lys Met Ser Lys Arg Glu Ala Ser
             85                  90                  95

Leu Ile Leu Gly Val Ser Pro Ser Ala Gly Lys Ala Lys Ile Arg Thr
        100                 105                 110

Ala His Lys Arg Ile Met Ile Leu Asn His Pro Asp Lys Gly Gly Ser
        115                 120                 125

Pro Tyr Val Ala Ser Lys Ile Asn Glu Ala Lys Asp Leu Leu Glu Ala
    130                 135                 140

Ser Ser Lys Ala Asn
145

<210> SEQ ID NO 4
<211> LENGTH: 150
<212> TYPE: PRT
<213> ORGANISM: Homo sapiens

<400> SEQUENCE: 4

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125

Gly Ser Pro Tyr Val Ala Ala Lys Ile Asn Glu Ala Lys Asp Leu Leu
    130                 135                 140

Glu Thr Thr Thr Lys His
145                 150

<210> SEQ ID NO 5
<211> LENGTH: 2404
<212> TYPE: DNA
<213> ORGANISM: Homo sapiens
<220> FEATURE:
<221> NAME/KEY: misc_feature
<222> LOCATION: (1)..(2404)
<223> OTHER INFORMATION: Homo sapiens DnaJ (Hsp40) homolog, subfamily C,
      member 15, mRNA (cDNA clone MGC:110875 IMAGE:30530999), complete
      cds GENBANK Accession No. BC095400.1

<400> SEQUENCE: 5
agtctccggg ccgccttgcc atggctgccc gtggtgtcat cgctccagtt ggcgagagtt      60
tgcgctacgc tgagtacttg cagccctcgg ccaaacggcc agacgccgac gtcgaccagc     120
agagactggt aagaagtttg atagctgtag gcctgggtgt tgcagctctt gcatttgcag     180
gtcgctacgc atttcggatc tggaaacctc tagaacaagt tatcacagaa actgcaaaga     240
agatttcaac tcctagcttt tcatcctact ataaaggagg atttgaacag aaaatgagta     300
ggcgagaagc tggtcttatt ttaggtgtaa gcccatctgc tggcaaggct aagattagaa     360
```

```
cagctcatag gagagtcatg attttgaatc acccagataa aggtggatct ccttacgtag    420
cagccaaaat aaatgaagca aaagacttgc tagaaacaac caccaaacat tgatgcttaa    480
ggaccacact gaaggaaaaa aaaagagggg acttcaaaaa aaaaaaaaaa gccctgcaaa    540
atattctaaa acatggtctt cttaattttc tatatggatt gaccacagtc ttatcttcca    600
ccattaagct gtataacaat aaaatgttaa tagtcttgct ttttattatc ttttaaagat    660
ctccttaaat tctataactg atcttttttc ttattttgtt tgtgacattc atacattttt    720 aagattttg ttatgttctg aattcccccc tacacacaca cacacacaca cacacacaca    780
cgtgcaaaaa atatgatcaa gaatgcaatt gggatttgtg agcaatgagt agacctctta    840
ttgtttatat ttgtaccctc attgtcaatt ttttttttagg gaatttggga ctctgcctat    900
ataaggtgtt ttaaatgtct tgagaacaag cactggctga tacctcttgg agatatgatc    960
tgaaatgtaa tggaatttat taaatggtgt ttagtaaagt aggggttaag gacttgttaa   1020
agaaccccac tatctctgag acccctatagc caaagcatga ggacttggag agctactaaa   1080
atgattcagg tttacaaaat gagccctgtg aggaaaggtt gagagaagtc tgaggagttt   1140
gtatttaatt atagtcttcc agtactgtat attcattcat tactcattct acaaatattt   1200
attgacccct tttgatgtgc aaggcactat cgtgcgtccc ctgagagttg caagtatgaa   1260
gcagtcatgg atcatgaacc aaaggaactt atatgtagag aaggataaa tcacaaatag   1320 tgaatactgt tagatacaga tgatatattt taaaagttca aaggaagaaa agaatgtgtt   1380
aaacactgca tgagaggagg aataagtggc atagagctag gctttagaaa agaaaaatat   1440
tccgatacca tatgattggt gaggtaagtg ttattctgag atgagaatta gcagaaatag   1500
atatatcaat cggagtgatt agagtgcagg gtttctggaa agcaaggttt ggacagagtg   1560
gtcatcaaag gccagccctg tgacttacac tgcattaaat taatttctta gaacatagtc   1620
cctgatcatt atcactttac tattccaaag gtgagagaac agattcagat agagtgccag   1680
cattgtttcc cagtattcct ttacaaatct tgggttcatt ccaggtaaac tgaactactg   1740
cattgtttct atcttaaaat acttttttaga tatcctagat gcatctttca acttctaaca   1800
ttctgtagtt taggagttct caaccttggc attattgaca tgttaggcca ataaattttt   1860
tttgtgggag gtctcttgtg cgttttagat gattagcaat aatccctgac ctgttatcta   1920
ctaaagacta gtcgtttctc atcagttgtg acaacaaaaa tggttccaga tattgccaaa   1980
tgccctttag aggacagtaa tcgcccccag ttgagaacca tttcagtaaa actttaatta   2040
ctattttttc ttttggttta taaaataatg atcctgaatt aaattgatgg aaccttgaag   2100
tcgataaaat atatttcttg ctttaaagtc cccatacgtg tcctactaat tttctcatgc   2160
tttagtgttt tcacttttct cctgttatcc ttgtacctaa gaatgccatc ccaatcccca   2220
gatgtccacc tgcccaaagt ctaggcatag ctgaaggcca agctaaaatg tatccctctt   2280
tttctggtac atgcagcaaa agtaaatatga attatcagct ttctgagagc aggcattgta   2340
tctgtcttgt ttggtgttac attggcaccc aataaatatt tgttgagcga aaaaaaaaaa   2400
aaaa                                                                 2404
```

<210> SEQ ID NO 6
<211> LENGTH: 2792
<212> TYPE: DNA
<213> ORGANISM: Homo sapiens
<220> FEATURE:
<221> NAME/KEY: misc_feature
<222> LOCATION: (1)..(2792)
<223> OTHER INFORMATION: cDNA sequence

<400> SEQUENCE: 6

```
caccctcagg cactacagct agactccgag cttactgggc agtcatctga ttcgaccaac      60
atcagttcgc agggcttaag cccagtccct tacggcggcc tggggaggga ccaggcccaa     120
gtatataaag ctccctgagg gtccgcgttg gctttgcgcc tgtgagtgtg attcaagaac     180
gtcccagtgc ccttggctcc tttcggagtg tgaccccgtg cttgcacggg acacgttacc     240
cagctcgggt gagaagggta tcttccggga acctcgcctt taatagcaca acgagcgcag     300
agtccactgg atctgcgaga gaaaccgcg ctaactagtt tgtccctacg gccgcctcgt     360
agtcactgcc gcggcgcctt gagtctccgg gccgccttgc catggctgcc cgtggtgtca     420
tcgctccagt tggcgagagt ttgcgctacg ctgagtactt gcagccctcg gccaaacggc     480
cagacgccga cgtcgaccag cagagactgg taagaagttt gatagctgta ggactgggtg     540
ttgcagctct tgcatttgca ggtcgctacg catttcggat ctggaaacct ctagaacaag     600
ttatcacaga aactgcaaag aagatttcaa ctcctagctt ttcatcctac tataaaggag     660
gatttgaaca gaaaatgagt aggcgagaag ctggtcttat tttaggtgta agcccatctg     720
ctggcaaggc taagattaga acagctcata ggagagtcat gattttgaat cacccagata     780
aaggtggatc tccttacgta gcagccaaaa taatgaagc aaaagacttg ctagaaacaa     840
ccaccaaaca ttgatgctta aggaccacac tgaaggaaaa aaaagaggg gacttcgaaa     900
aaaaaaaaag ccctgcaaaa tattctaaaa catggtcttc ttaattttct atatggattg     960
accacagtct tatcttccac cattaagctg tataacaata aaatgttaat agtcttgctt    1020
tttattatct tttaaagatc tccttaaatt ctataactga tctttttttct tattttgttt    1080
gtgacattca tacattttta agattttttgt tatgttctga attcccccct acacacacac    1140
acacacacac acacacacac acgtgcaaaa aatatgatca agaatgcaat gggatttgt    1200
gagcaatgag tagacctctt attgtttata tttgtaccct cattgtcaat ttttttttag    1260
ggaatttggg actctgccta tataaggtgt tttaaatgtc ttgagaacaa gcactggctg    1320
atacctcttg gagatatgat ctgaaatgta atggaattta ttaaatggtg tttagtaaag    1380
taggggttaa ggacttgtta aagaacccca ctatctctga acccctatag ccaaagcatg    1440
aggacttgga gagctactaa aatgattcag gtttacaaaa tgagccctgt gaggaaaggt    1500
tgagagaagt ctgaggagtt tgtatttaat tatagtcttc cagtactgta tattcattca    1560
ttactcattc tacaaatatt tattgacccc ttttgatgtg caaggcacta tcgtgcgtcc    1620
cctgagagtt gcaagtatga agcagtcatg gatcatgaac caaaggaact tatatgtaga    1680
ggaaggataa atcacaaata gtgaatactg ttagatacag atgatatatt ttaaaagttc    1740
aaaggaagaa aagaatgtgt taaacactgc atgagaggag gaataagtgg catagagcta    1800
ggctttagaa aagaaaaata ttccgatacc atatgattgg tgaggtaagt gttattctga    1860
gatgagaatt agcagaaata gatatatcaa tcggagtgat tagagtgcag ggtttctgga    1920
aagcaaggtt tggacagagt ggtcatcaaa ggccagccct gtgacttaca ctgcattaaa    1980
ttaatttctt agaacatagt ccctgatcat tatcacttta ctattccaaa ggtgagagaa    2040
cagattcaga tagagtgcca gcattgtttc ccagtattcc tttacaaatc ttgggttcat    2100
tccaggtaaa ctgaactact gcattgtttc tatcttaaaa tacttttag atatcctaga    2160
tgcatcttc aacttctaac attctgtagt ttaggagttc tcaaccttgg cattattgac    2220
atgttaggcc aaataatttt ttttgtggga ggtctcttgt gcgttttaga tgattagcaa    2280
```

-continued

```
taatccctga cctgttatct actaaagact agtcgtttct catcagttgt gacaacaaaa    2340
atggttccag atattgccaa atgcccttta gaggacagta atcgccccca gttgagaacc    2400
atttcagtaa aactttaatt actattttt cttttggttt ataaataat gatcctgaat      2460 taaattgatg gaaccttgaa gtcgataaaa tatatttctt gctttaaagt ccccatacgt    2520
gtcctactaa ttttctcatg ctttagtgtt ttcactttc tcctgttatc cttgtaccta    2580
agaatgccat cccaatcccc agatgtccac ctgcccaaag tctaggcata gctgaaggcc    2640
aagctaaaat gtatccctct ttttctggta catgcagcaa aagtaatatg aattatcagc    2700
tttctgagag caggcattgt atctgtcttg tttggtgtta cattggcacc caataaatat    2760
ttgttgagtg aatgaaaaaa aaaaaaaaaa aa                                  2792
```

<210> SEQ ID NO 7
<211> LENGTH: 19
<212> TYPE: DNA
<213> ORGANISM: Homo sapiens
<220> FEATURE:
<221> NAME/KEY: misc_RNA
<222> LOCATION: (1)..(19)
<223> OTHER INFORMATION: siRNA

<400> SEQUENCE: 7
gaagatttca actcctagc                                                   19

<210> SEQ ID NO 8
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 8
ggcgagaagc tggtcttatt t                                                21

<210> SEQ ID NO 9
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 9
gctaagatta gaacagctca t                                                21

<210> SEQ ID NO 10
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 10
gctcatagga gagtcatgat t                                                21

<210> SEQ ID NO 11
<211> LENGTH: 21
<212> TYPE: DNA
<213> ORGANISM: Homo sapiens

```
<220> FEATURE:
<221> NAME/KEY: misc_RNA
<222> LOCATION: (1)..(21)
<223> OTHER INFORMATION: siRNA

<400> SEQUENCE: 11
tttgggactc tgcctatata a                                              21

<210> SEQ ID NO 12
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 12
gttgcagctc ttgcatttgc a                                              21

<210> SEQ ID NO 13
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 13
ctacgcattt cggatctgga a                                              21

<210> SEQ ID NO 14
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 14
gcagggactg gtaagaagtt t                                              21

<210> SEQ ID NO 15
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 15
gttgcagctc ttgcatttgc a                                              21

<210> SEQ ID NO 16
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 16
cagataaagg tggatctcct t                                              21
```

```
<210> SEQ ID NO 17
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 17
gctcatagga gagtcatgat t                                              21

<210> SEQ ID NO 18
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 18
gctaagatta gaacagctca t                                              21

<210> SEQ ID NO 19
<211> LENGTH: 19
<212> TYPE: DNA
<213> ORGANISM: Homo sapiens
<220> FEATURE:
<221> NAME/KEY: misc_RNA
<222> LOCATION: (1)..(19)
<223> OTHER INFORMATION: siRNA

<400> SEQUENCE: 19
gtttgatagc tgtaggact                                                 19

<210> SEQ ID NO 20
<211> LENGTH: 19
<212> TYPE: DNA
<213> ORGANISM: Homo sapiens
<220> FEATURE:
<221> NAME/KEY: misc_RNA
<222> LOCATION: (1)..(19)
<223> OTHER INFORMATION: siRNA

<400> SEQUENCE: 20
tcacccagat aaaggtgga                                                 19

<210> SEQ ID NO 21
<211> LENGTH: 21
<212> TYPE: DNA
<213> ORGANISM: Homo sapiens
<220> FEATURE:
<221> NAME/KEY: misc_RNA
<222> LOCATION: (1)..(21)
<223> OTHER INFORMATION: siRNA

<400> SEQUENCE: 21
gaagatttca actcctagct t                                              21

<210> SEQ ID NO 22
<211> LENGTH: 19
<212> TYPE: DNA
<213> ORGANISM: Mus musculus
<220> FEATURE:
<221> NAME/KEY: misc_RNA
<222> LOCATION: (1)..(19)
<223> OTHER INFORMATION: siRNA
```

```
<400> SEQUENCE: 22
gcgagaggct agtcttatt                                                    19

<210> SEQ ID NO 23
<211> LENGTH: 671
<212> TYPE: DNA
<213> ORGANISM: Mus musculus
<220> FEATURE:
<221> NAME/KEY: misc_feature
<222> LOCATION: (1)..(671)
<223> OTHER INFORMATION: cDNA sequence

<400> SEQUENCE: 23
tcggagtcct gcagtgccat ggctaccggt ggcggcgtga cctccagaga ggggctgcgc        60
tacgccgaat acctgcctcc ttctgcccaa aggtcggacg ccgacatcga ccacacagcg       120
gggagaaggt tgctagctgt aggactaggt gttgcagctg ttgcatttgc aggtcgctat       180
gcatttcaga tctggaaacc tctagaacaa gtaatcacgg caacagcaag gaagatttcc       240
tctccaagct tttcatccta ctataaagga ggattcgagc agaaaatgag taagcgagag       300
gctagtctta ttttaggtgt aagcccatct gctggcaagg ccaagattag aacagcacac       360
aagagaatta tgattttaaa ccatccagac aaaggtggat ctccttactt agcatccaaa       420
ataaatgaag caaagattt gctcgaagca tccagcaaag ctaactgatg ctaaaggact        480
gtacataccg agggaaaatg gaacaaacgc acagctgtaa aagtccttca gaagaatgtg       540
gcacgtggtc gtgttccata ctgacccagt ctgttttctg tcattaagtg tgcagcaata       600
aaagcctggc agccttgcag ccttggtctg gcagggactt catccgtcaa aaaaaaaaa        660 aaaaaaaaaa a                                                           671
```